(12) United States Patent
Hart et al.

(10) Patent No.: US 7,951,076 B2
(45) Date of Patent: May 31, 2011

(54) SURGICAL ACCESS SYSTEM

(75) Inventors: Charles C. Hart, Summerville, SC (US); Edward D. Pingleton, San Juan Capistrano, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 1597 days.

(21) Appl. No.: 11/245,709

(22) Filed: Oct. 7, 2005

(65) Prior Publication Data

US 2006/0084842 A1    Apr. 20, 2006

Related U.S. Application Data

(63) Continuation of application No. 10/927,551, filed on Aug. 25, 2004, now abandoned.

(51) Int. Cl.
*A61B 1/32*  (2006.01)
(52) U.S. Cl. ........................................ 600/206
(58) Field of Classification Search .......... 600/204–210; 604/167.01–167.04; 251/205, 208
See application file for complete search history.

(56) References Cited

U.S. PATENT DOCUMENTS

| | | |
|---|---|---|
| 558,364 A | 4/1896 | Doolittle |
| 1,157,202 A | 10/1915 | Bates et al. |
| 1,810,466 A | 6/1931 | Deutsch |
| 2,305,289 A | 12/1942 | Coburg |
| 2,478,586 A | 8/1949 | Krapp |
| 2,812,758 A | 11/1957 | Blumenschein |
| 2,835,253 A | 5/1958 | Borgeson |
| 2,853,075 A | 9/1958 | Hoffman et al. |
| 3,039,468 A | 6/1962 | Price |
| 3,111,943 A | 11/1963 | Orndorff |
| 3,195,934 A | 7/1965 | Parrish |
| 3,244,169 A | 4/1966 | Baxter |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,416,520 A | 12/1968 | Creager, Jr. |

(Continued)

FOREIGN PATENT DOCUMENTS

EP    1 125 552    8/2001

(Continued)

OTHER PUBLICATIONS

Co-Pending U.S. Appl. No. 10/381,220, filed Mar. 20, 2003; Title: Surgical Access Apparatus and Method.

(Continued)

*Primary Examiner* — Anu Ramana
(74) *Attorney, Agent, or Firm* — Patrick Y. Ikehara; Pui Tong Ho; David G. Majdali

(57) ABSTRACT

A surgical access device adapted for disposition relative to an incision in a patient comprising a valve including a plurality of overlapping sheets defining an access channel, and a ring having an inner diameter for holding the valve by fixing each of the overlapping sheets along a portion of the perimeter is described. The access channel extends into communication with the incision in the patient. Each of the overlapping sheets includes a portion of the perimeter that is not fixed to the inner diameter of the ring, which provide open edges defining the access channel. The open edges slightly overlap at the center of the ring.

21 Claims, 22 Drawing Sheets

U.S. PATENT DOCUMENTS

| | | | |
|---|---|---|---|
| 3,447,533 A | 6/1969 | Spicer | 128/1 |
| 3,523,534 A | 8/1970 | Nolan | |
| 3,717,151 A | 2/1973 | Collett | |
| 3,831,583 A | 8/1974 | Edmunds et al. | |
| 3,841,332 A | 10/1974 | Treacle | |
| 3,850,172 A | 11/1974 | Cazalis | |
| 3,856,021 A | 12/1974 | McIntosh | |
| 3,860,274 A | 1/1975 | Ledstrom et al. | |
| 4,024,872 A | 5/1977 | Muldoon | |
| 4,043,328 A | 8/1977 | Cawood, Jr. et al. | |
| 4,069,913 A | 1/1978 | Harrigan | |
| 4,083,370 A | 4/1978 | Taylor | |
| 4,188,945 A | 2/1980 | Wenander | |
| 4,217,664 A | 8/1980 | Faso | |
| 4,222,126 A | 9/1980 | Boretos et al. | |
| 4,254,973 A | 3/1981 | Benjamin | |
| 4,338,937 A | 7/1982 | Lerman | |
| 4,367,728 A | 1/1983 | Mutke | |
| 4,369,284 A | 1/1983 | Chen | |
| 4,454,873 A | 6/1984 | Laufenberg et al. | |
| 4,475,548 A | 10/1984 | Muto | |
| 4,550,713 A | 11/1985 | Hyman | |
| 4,553,537 A | 11/1985 | Rosenberg | |
| 4,691,942 A | 9/1987 | Ford | |
| 4,714,749 A | 12/1987 | Hughes et al. | |
| 4,755,170 A | 7/1988 | Golden | |
| 4,777,943 A | 10/1988 | Chvapil | |
| 4,798,594 A | 1/1989 | Hillstead | |
| 4,802,694 A | 2/1989 | Vargo | |
| 4,842,931 A | 6/1989 | Zook | |
| 4,856,502 A | 8/1989 | Ersfeld et al. | |
| 4,863,438 A | 9/1989 | Gauderer et al. | |
| 4,889,107 A | 12/1989 | Kaufman | |
| 4,895,565 A | 1/1990 | Hillstead | |
| 4,903,710 A | 2/1990 | Jessamine et al. | |
| 4,911,974 A | 3/1990 | Shimizu et al. | |
| 4,926,882 A | 5/1990 | Lawrence | |
| 4,950,223 A | 8/1990 | Silvanov | |
| 4,984,564 A | 1/1991 | Yuen | |
| 4,991,593 A | 2/1991 | LeVahn | |
| 4,998,538 A | 3/1991 | Charowsky et al. | |
| 5,000,745 A * | 3/1991 | Guest et al. | 604/256 |
| 5,015,228 A | 5/1991 | Columbus et al. | 604/51 |
| 5,037,379 A | 8/1991 | Clayman et al. | |
| 5,159,921 A | 11/1992 | Hoover | |
| 5,178,162 A | 1/1993 | Bose | |
| 5,180,365 A * | 1/1993 | Ensminger et al. | 604/288.03 |
| 5,192,301 A | 3/1993 | Kamiya et al. | 606/213 |
| 5,207,656 A | 5/1993 | Kranys | |
| 5,213,114 A | 5/1993 | Bailey, Jr. | |
| 5,259,366 A | 11/1993 | Reydel et al. | |
| 5,262,468 A | 11/1993 | Chen | |
| 5,299,582 A | 4/1994 | Potts | |
| 5,316,541 A | 5/1994 | Fischer | |
| 5,336,708 A | 8/1994 | Chen | |
| 5,342,315 A | 8/1994 | Rowe et al. | |
| 5,350,364 A | 9/1994 | Stephens et al. | |
| 5,353,786 A | 10/1994 | Wilk | |
| 5,366,445 A | 11/1994 | Haber et al. | |
| 5,366,478 A | 11/1994 | Brinkerhoff et al. | 660/213 |
| 5,368,545 A | 11/1994 | Schaller et al. | 600/37 |
| 5,380,288 A | 1/1995 | Hart et al. | |
| 5,385,552 A | 1/1995 | Haber et al. | |
| 5,389,080 A | 2/1995 | Yoon | |
| 5,389,081 A | 2/1995 | Castro | |
| 5,407,433 A | 4/1995 | Loomas | |
| 5,429,609 A | 7/1995 | Yoon | |
| 5,437,683 A | 8/1995 | Neumann et al. | |
| 5,441,486 A | 8/1995 | Yoon | |
| 5,456,284 A | 10/1995 | Ryan et al. | |
| 5,460,616 A | 10/1995 | Weinstein et al. | |
| 5,476,475 A | 12/1995 | Gadberry | |
| 5,480,410 A | 1/1996 | Cuschieri et al. | 606/213 |
| 5,486,426 A | 1/1996 | McGee et al. | |
| 5,492,304 A | 2/1996 | Smith et al. | |
| 5,496,280 A | 3/1996 | Vandenbroek et al. | |
| 5,503,112 A | 4/1996 | Luhman et al. | |
| 5,508,334 A | 4/1996 | Chen | |
| 5,514,133 A | 5/1996 | Golub et al. | 606/1 |
| 5,518,278 A | 5/1996 | Sampson | |
| 5,522,791 A | 6/1996 | Leyva | |
| 5,524,644 A | 6/1996 | Crook | |
| 5,531,758 A | 7/1996 | Uschold | |
| 5,545,179 A | 8/1996 | Williamson, IV | 606/213 |
| 5,562,677 A | 10/1996 | Hildwein et al. | |
| 5,603,702 A | 2/1997 | Smith et al. | |
| 5,628,732 A | 5/1997 | Antoon, Jr. et al. | |
| 5,632,284 A | 5/1997 | Graether | |
| 5,634,911 A | 6/1997 | Hermann et al. | |
| 5,634,936 A | 6/1997 | Linden et al. | 606/213 |
| 5,634,937 A | 6/1997 | Mollenauer et al. | 606/213 |
| 5,636,645 A | 6/1997 | Ou | 28/898 |
| 5,640,977 A | 6/1997 | Leahy et al. | 128/897 |
| 5,649,550 A | 7/1997 | Crook | |
| 5,653,705 A | 8/1997 | de la Torre et al. | |
| 5,672,168 A | 9/1997 | de la Torre et al. | 106/1 |
| 5,681,341 A | 10/1997 | Lunsford et al. | |
| 5,709,664 A | 1/1998 | Vandenbroek et al. | |
| 5,720,730 A | 2/1998 | Blake, III | |
| 5,728,103 A | 3/1998 | Picha et al. | |
| 5,741,298 A | 4/1998 | MacLeod | 606/213 |
| 5,753,150 A | 5/1998 | Martin et al. | |
| 5,760,117 A | 6/1998 | Chen | |
| 5,782,817 A | 7/1998 | Franzel et al. | |
| 5,788,676 A | 8/1998 | Yoon | |
| 5,792,119 A | 8/1998 | Marx | |
| 5,795,290 A | 8/1998 | Bridges | 600/210 |
| 5,803,919 A | 9/1998 | Hart et al. | |
| 5,803,921 A | 9/1998 | Bonadio | 606/1 |
| 5,803,923 A | 9/1998 | Singh-Derewa et al. | |
| 5,810,721 A | 9/1998 | Mueller et al. | |
| 5,813,409 A | 9/1998 | Leahy et al. | 128/897 |
| 5,814,026 A | 9/1998 | Yoon | |
| 5,819,375 A | 10/1998 | Kastner | |
| 5,832,925 A | 11/1998 | Rothrum | |
| 5,841,298 A | 11/1998 | Huang | |
| 5,853,395 A | 12/1998 | Crook et al. | |
| 5,865,729 A | 2/1999 | Meehan et al. | |
| 5,865,807 A | 2/1999 | Blake, III | |
| 5,871,474 A | 2/1999 | Hermann | |
| 5,895,377 A | 4/1999 | Smith et al. | |
| 5,899,208 A | 5/1999 | Bonadio | 128/897 |
| 5,904,703 A | 5/1999 | Gilson | 606/213 |
| 5,906,577 A | 5/1999 | Beane et al. | |
| 5,919,476 A | 7/1999 | Fischer et al. | |
| 5,947,922 A | 9/1999 | MacLeod | 604/27 |
| 5,951,588 A | 9/1999 | Moenning | |
| 5,957,888 A | 9/1999 | Hinchliffe | |
| 5,957,913 A | 9/1999 | de la Torre | |
| 5,962,572 A | 10/1999 | Chen | |
| 5,964,781 A | 10/1999 | Mollenauer et al. | 606/213 |
| 5,989,233 A | 11/1999 | Yoon | |
| 5,989,266 A | 11/1999 | Foster | |
| 5,993,471 A | 11/1999 | Riza et al. | |
| 5,993,485 A | 11/1999 | Beckers | |
| 5,997,515 A | 12/1999 | de la Torre et al. | 604/256 |
| 6,010,494 A | 1/2000 | Schafer et al. | |
| 6,024,736 A | 2/2000 | de la Torre | |
| 6,025,067 A | 2/2000 | Fay | |
| 6,033,426 A | 3/2000 | Kaji | 606/213 |
| 6,033,428 A | 3/2000 | Sardella | 606/213 |
| 6,035,559 A | 3/2000 | Freed et al. | |
| 6,045,535 A | 4/2000 | Ben Nun | |
| 6,053,934 A | 4/2000 | Andrews | |
| 6,077,288 A | 6/2000 | Shimomura | |
| 6,090,043 A | 7/2000 | Austin et al. | |
| 6,110,154 A | 8/2000 | Shimomura et al. | |
| 6,142,935 A | 11/2000 | Flom | |
| 6,142,936 A | 11/2000 | Beane et al. | |
| 6,149,642 A | 11/2000 | Gerhart et al. | |
| 6,150,608 A | 11/2000 | Wambeke et al. | |
| 6,162,172 A | 12/2000 | Cosgrove et al. | 600/208 |
| 6,224,612 B1 | 5/2001 | Bates | |
| 6,238,373 B1 | 5/2001 | de la Torre | |
| 6,254,533 B1 | 7/2001 | Fadem et al. | |
| 6,254,534 B1 | 7/2001 | Butler | |
| 6,276,661 B1 | 8/2001 | Laird | |

| | | |
|---|---|---|
| 6,287,280 B1 | 9/2001 | Lampropoulos |
| 6,319,246 B1 | 11/2001 | de la Torre |
| 6,325,384 B1 | 12/2001 | Berry, Sr. et al. |
| 6,382,211 B1 | 5/2002 | Crook |
| 6,383,162 B1 | 5/2002 | Sugarbaker |
| 6,413,244 B1 | 7/2002 | Bestetti et al. |
| 6,440,063 B1 | 8/2002 | Beane et al. |
| 6,450,983 B1 | 9/2002 | Rambo |
| 6,482,181 B1 | 11/2002 | Racenet et al. |
| 6,485,435 B1 | 11/2002 | Bakal |
| 6,533,734 B1 | 3/2003 | Corley, III et al. |
| 6,551,344 B2 | 4/2003 | Thill |
| 6,569,120 B1 | 5/2003 | Green et al. |
| 6,578,577 B2 | 6/2003 | Bonadio et al. |
| 6,579,281 B2 | 6/2003 | Palmer et al. |
| 6,582,364 B2 | 6/2003 | Butler et al. |
| 6,589,167 B1 | 7/2003 | Shimomura et al. |
| 6,589,211 B1 | 7/2003 | MacLeod |
| 6,613,952 B2 | 9/2003 | Rambo |
| 6,623,426 B2 | 9/2003 | Bonadio et al. |
| 6,663,598 B1 * | 12/2003 | Carrillo et al. ............ 604/167.01 |
| 6,702,787 B2 | 3/2004 | Racenet et al. |
| 6,723,044 B2 | 4/2004 | Pulford et al. |
| 6,814,078 B2 | 11/2004 | Crook |
| 6,846,287 B2 | 1/2005 | Bonadio et al. |
| 6,866,861 B1 | 3/2005 | Luhman |
| 6,895,965 B2 | 5/2005 | Scarberry et al. |
| 6,902,541 B2 | 6/2005 | McNally et al. |
| 6,908,430 B2 | 6/2005 | Caldwell et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,997,909 B2 | 2/2006 | Goldberg |
| 7,033,319 B2 | 4/2006 | Pulford et al. |
| 7,052,454 B2 | 5/2006 | Taylor |
| 7,081,089 B2 | 7/2006 | Bonadio et al. |
| 7,214,185 B1 | 5/2007 | Rosney |
| 7,371,227 B2 | 5/2008 | Zeiner |
| 7,481,795 B2 | 1/2009 | Thompson et al. |
| 2001/0037053 A1 | 11/2001 | Bonadio et al. |
| 2001/0047188 A1 | 11/2001 | Bonadio et al. |
| 2002/0002324 A1 | 1/2002 | McManus |
| 2002/0038077 A1 | 3/2002 | de la Torre |
| 2002/0072762 A1 | 6/2002 | Bonadio et al. |
| 2002/0156432 A1 | 10/2002 | Racenet |
| 2003/0040711 A1 | 2/2003 | Racenet et al. |
| 2003/0139756 A1 | 7/2003 | Brustad |
| 2003/0187376 A1 | 10/2003 | Rambo |
| 2003/0192553 A1 | 10/2003 | Rambo |
| 2003/0225392 A1 | 12/2003 | McMichael et al. |
| 2004/0015185 A1 | 1/2004 | Ewers et al. |
| 2004/0049099 A1 | 3/2004 | Ewers et al. |
| 2004/0049100 A1 | 3/2004 | Butler et al. |
| 2004/0054353 A1 | 3/2004 | Taylor |
| 2004/0073090 A1 | 4/2004 | Butler et al. |
| 2004/0092796 A1 | 5/2004 | Butler et al. |
| 2004/0106942 A1 | 6/2004 | Taylor et al. |
| 2004/0127772 A1 | 7/2004 | Ewers et al. |
| 2004/0154624 A1 | 8/2004 | Bonadio et al. |
| 2004/0167559 A1 | 8/2004 | Taylor et al. |
| 2004/0173218 A1 | 9/2004 | Yamada et al. |
| 2004/0215063 A1 | 10/2004 | Bonadio et al. |
| 2004/0254426 A1 | 12/2004 | Wenchell |
| 2004/0267096 A1 | 12/2004 | Caldwell et al. |
| 2005/0020884 A1 | 1/2005 | Hart et al. |
| 2005/0033246 A1 | 2/2005 | Ahlberg et al. |
| 2005/0059865 A1 | 3/2005 | Kahle et al. |
| 2005/0090717 A1 | 4/2005 | Bonadio et al. |
| 2005/0148823 A1 | 7/2005 | Vaugh et al. |
| 2005/0155611 A1 | 7/2005 | Vaugh et al. |
| 2005/0197537 A1 | 9/2005 | Bonadio et al. |
| 2005/0222582 A1 | 10/2005 | Wenchell |
| 2005/0241647 A1 | 11/2005 | Nguyen et al. |
| 2005/0261720 A1 | 11/2005 | Caldwell et al. |
| 2005/0267419 A1 | 12/2005 | Smith |
| 2005/0283050 A1 | 12/2005 | Gundlapalli et al. |
| 2005/0288558 A1 | 12/2005 | Ewers et al. |
| 2006/0030755 A1 | 2/2006 | Ewers et al. |
| 2006/0047284 A1 | 3/2006 | Gresham |
| 2006/0052669 A1 | 3/2006 | Hart |
| 2006/0084842 A1 | 4/2006 | Hart et al. |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161050 A1 | 7/2006 | Butler et al. |

FOREIGN PATENT DOCUMENTS

| | | |
|---|---|---|
| IE | 930649 | 9/1993 |
| IE | 930650 | 9/1993 |
| IE | S940150 | 2/1994 |
| IE | 940613 | 8/1994 |
| IE | S940960 | 12/1994 |
| IE | S950055 | 1/1995 |
| IE | S950266 | 4/1995 |
| IE | S960196 | 8/1997 |
| IE | S970810 | 11/1997 |
| IE | 990218 | 11/2000 |
| IE | 990219 | 11/2000 |
| IE | 990220 | 11/2000 |
| IE | 990660 | 2/2001 |
| IE | 990795 | 3/2001 |
| JP | 2002-28163 | 1/2002 |
| JP | 02003 235879 A | 8/2003 |
| WO | WO95/07056 | 3/1995 |
| WO | WO95/22289 | 8/1995 |
| WO | WO 95/24864 | 9/1995 |
| WO | WO 95/27468 | 10/1995 |
| WO | WO 97/11642 | 4/1997 |
| WO | WO 98/19853 | 5/1998 |
| WO | WO 98/35614 | 8/1998 |
| WO | WO 98/48724 | 11/1998 |
| WO | WO 99/15068 | 4/1999 |
| WO | WO 99/25268 | 5/1999 |
| WO | WO 00/32116 | 6/2000 |
| WO | WO 0035356 | 6/2000 |
| WO | WO 00/32120 | 8/2000 |
| WO | WO00/54675 | 9/2000 |
| WO | WO00/54676 | 9/2000 |
| WO | WO00/54677 | 9/2000 |
| WO | WO01/08581 | 2/2001 |
| WO | WO 01/26559 | 4/2001 |
| WO | WO02/034108 | 5/2002 |
| WO | WO 03/032819 A1 | 4/2003 |
| WO | WO03/034908 | 5/2003 |
| WO | WO03/061480 | 7/2003 |
| WO | WO 03/077726 | 9/2003 |
| WO | WO 03/103548 | 12/2003 |
| WO | WO 2004/075730 A2 | 9/2004 |
| WO | WO 2004/075730 A3 | 9/2004 |
| WO | WO 2004/075741 A2 | 9/2004 |
| WO | WO 2004/075741 A3 | 9/2004 |
| WO | WO 2004/075930 A2 | 9/2004 |
| WO | WO 2004/075930 A3 | 9/2004 |
| WO | WO 2005/034766 A2 | 4/2005 |

OTHER PUBLICATIONS

Co-Pending U.S. Appl. No. 10/516,198, filed Nov. 30, 2004; Title: Wound Retractor.

Co-Pending U.S. Appl. No. 10/927,551, filed Aug. 25, 2004; Title: Surgical Access System.

Co-Pending U.S. Appl. No. 11/244,647, filed Oct. 5, 2005; Title: Surgical Access Apparatus and Method.

Co-Pending U.S. Appl. No. 11/755,305, filed May 30, 2007; Title: Wound Retraction Apparatus and Method.

Co-Pending U.S. Appl. No. 11/330,661, filed Jan. 12, 2006; Title: Sealed Surgical Access Device.

Co-Pending U.S. Appl. No. 11/548,746, filed Oct. 12, 2006; Title: Method of Making a Hand Access Laparoscopic Device.

Co-Pending U.S. Appl. No. 11/548,758, filed Oct. 12, 2006; Title: Split Hoop Wound Retractor With Gel Pad.

Co-Pending U.S. Appl. No. 11/548,765, filed Oct. 12, 2006; Title: Split Hoop Wound Retractor.

Co-Pending U.S. Appl. No. 11/548,767, filed Oct. 12, 2006; Title: Circular Surgical Retractor.

Co-Pending U.S. Appl. No. 11/548,781, filed Oct. 12, 2006; Title: Wound Retractor With Gel Cap.

Co-Pending U.S. Appl. No. 11/548,955, filed Oct. 12, 2006; Title: Hand Access Laparoscopic Device.

Co-Pending U.S. Appl. No. 11/564,409, filed Nov. 29, 2006; Title: Surgical Instrument Access Device.

European Patent Office, Supplementary European Search Report for European Application No. EP 01 97 3379, dated Jul. 5, 2007, based on International Patent Application No. PCT/US01/29682, filed Sep. 21, 2001.

US 5,344,646, Chen. (withdrawn).

The International Bureau of WIPO, International Preliminary Report on Patentability, dated Aug. 29, 2006, for international application No. PCT/US2004/028250.

The International Bureau of WIPO, International Preliminary Report on Patentability dated Apr. 16, 2008 for PCT Application No. PCT/US2006/039799.

The International Bureau of WIPO, International Preliminary Report on Patentability for International Application No. PCT/US2006/039800 dated Apr. 16, 2008.

Co-Pending U.S. Appl. No. 12/108,400, filed Oct. 7, 2005 Title Surgical Access System.

Co-Pending U.S. Appl. No. 11/245,709, filed Oct. 7, 2005; Title Surgical Access System.

US Patent Office, International Search Report and The Written Opinion of the International Searching Authority for PCT Application No. PCT/US2004/05484.

European Patent Office, International Search Report and The Written Opinion of the International Searching Authority for PCT Application No. PCT/US2006/039799 mailed Mar. 27, 2007.

European Patent Office, International Search Report and The Written Opinion of the International Searching Authority for PCT Application No. PCT/US2006/039800 mailed Apr. 16, 2007.

Dexterity Protractor Instruction Manual by Dexterity Surgical, Inc.

European Patent Office, International Search Report and Written Opinion of the International Searching Authority for International Application No. PCT/US2006/039883, mailed Jan. 31, 2007.

European Patent Office, International Search Report and Written Opinion of the International Searching Authority for International Application No. PCT/US2006/039905, mailed Jan. 17, 2007.

European Patent Office, International Search Report and The Written Opinion of the International Searching Authority for International Application No. PCT/US2006/040073, Jan. 26, 2007.

European Patent Office, International Search Report and The Written Opinion of the International Searching Authority for International Application No. PCT/US2006/040154, maile.

International Search Report and Written Opinion of the International Searching Authority for PCT application No. PCT/US01/29682.

Horigane, et al., Technical Note: Development of a Duodoenal Cannula for Sheep, Journal of Animal Science, Apr. 1992, vol. 70, Issue 4, pp. 1216-1219.

Yamazaki et al., Diurnal Changes in the Composition of Abomasal Digesta in Fasted and Fed Sheep, The Tohoku Journal of Argircultural Research, Mar. 1987, vol. 37, No. 3-4, pp. 49-58.

Neil Sheehan, Supplemental Expert Report of Neil Sheehan, Re: U.S. Patent No. 5,741,298, United States District Court for the Central District of California, Civil Action No. SACV 03-1322 JVS, Aug. 9, 2005.

Technical Note: Development of a Duodenal Cannula for Sheep, Faculty of Agriculture and School of Medicine Tohoku University, Sendai 981, Japan.

Silicone Rumen Cannula with a Soft Cylindrical Part and a Hard Flange, Journal of Dairy Science, Nov. 1989, vol. 72, No. 11, Faculty of Agriculture, Tohoku University.

Cannulation of the rumen in cattle and buffaloes, Australian Veterinary Journal, vol. 66, Aug. 1989 No. 8.

Diurnal Changes in the Composition of Abomasal Digesta in Fasted and Fed Sheep, The Tohoku Journal of Agricultural Research, vol. 37, No. 3-4, Mar. 1987.

* cited by examiner

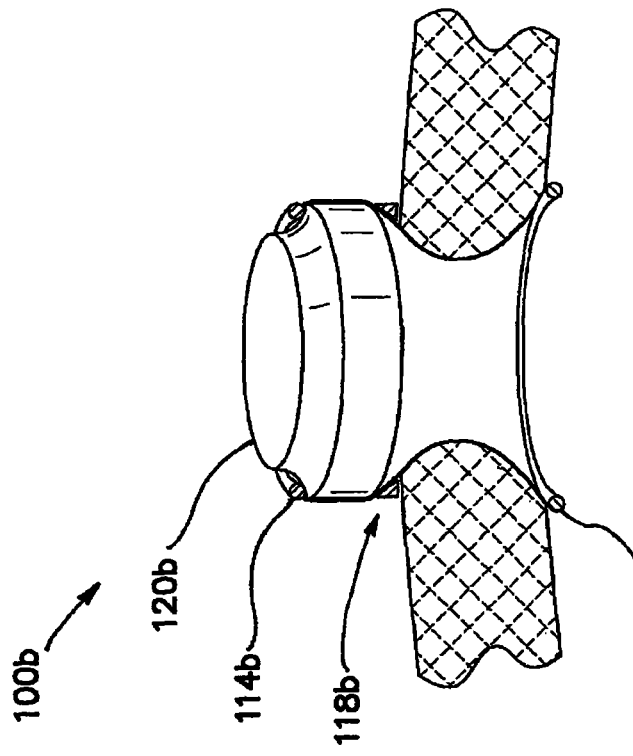
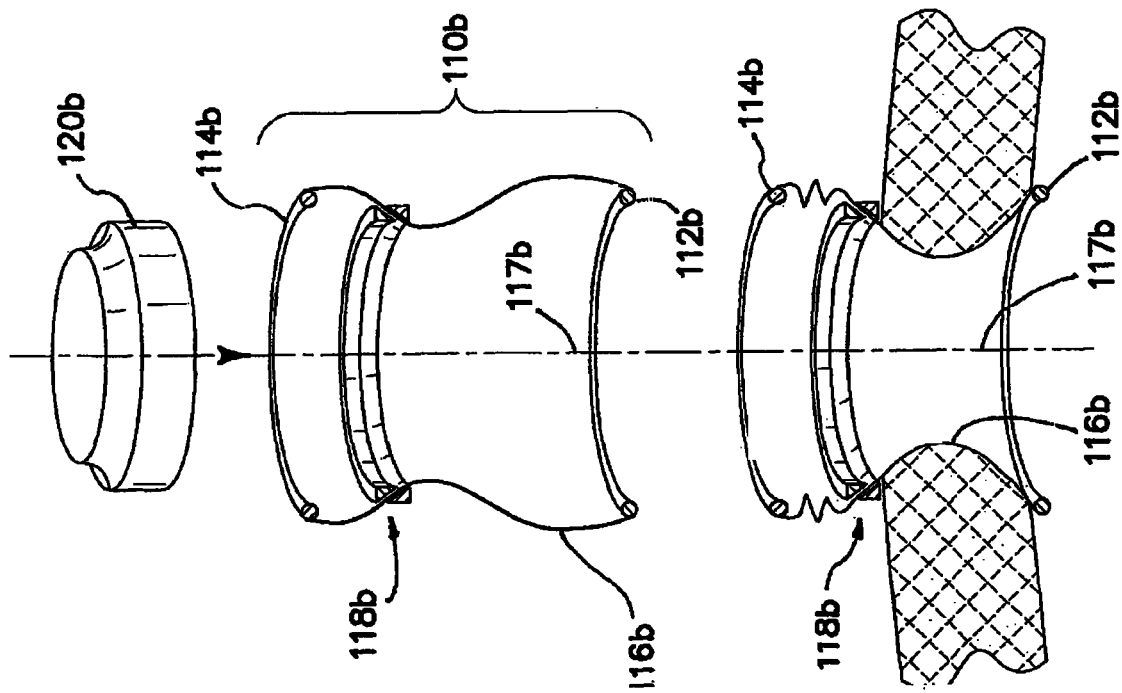
FIG. 3B
FIG. 3A

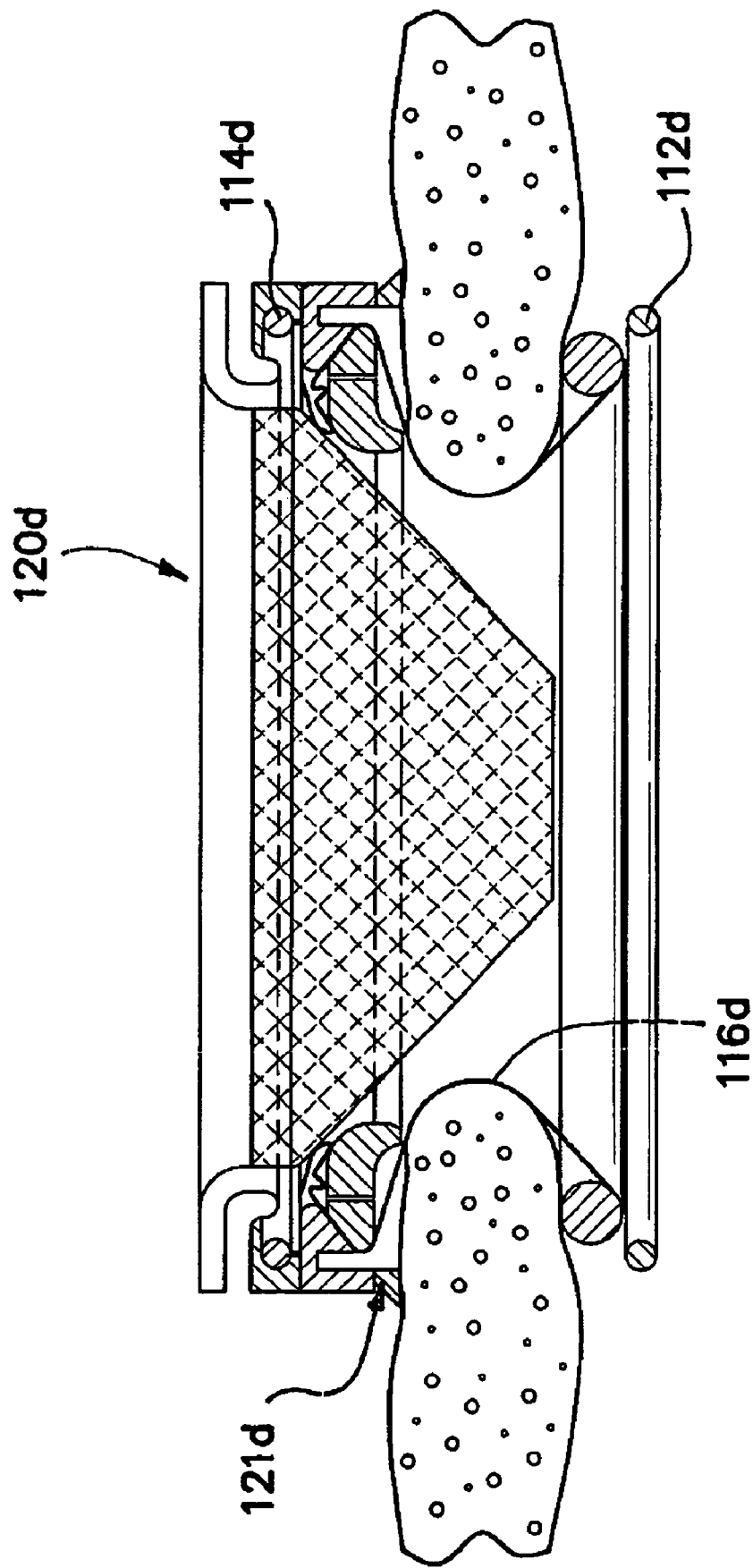

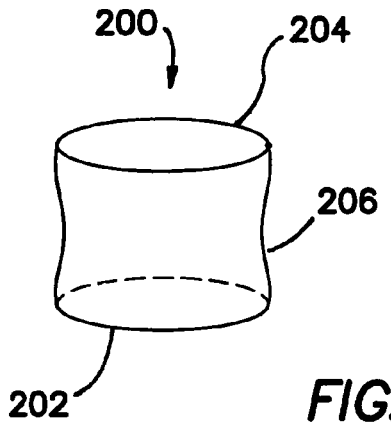
FIG. 7A
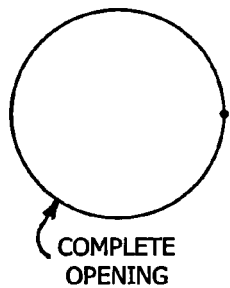
COMPLETE OPENING
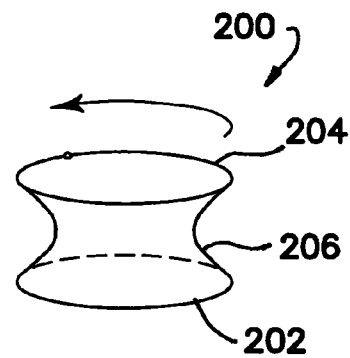
FIG. 7B
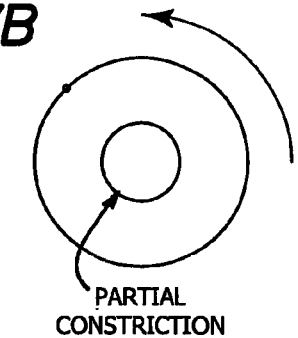
PARTIAL CONSTRICTION
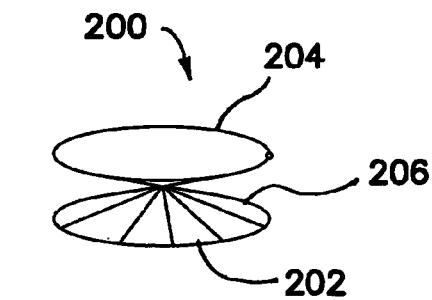
FIG. 7C
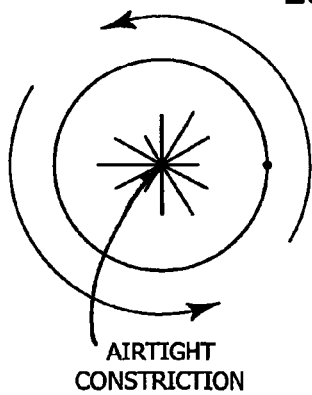
AIRTIGHT CONSTRICTION

DEROTATION

ROTATION

US 7,951,076 B2

SURGICAL ACCESS SYSTEM

CROSS-REFERENCE TO RELATED APPLICATIONS

This is a continuation application claiming the priority of U.S. Continuation application Ser. No. 10/927,551, entitled "Surgical Access System," filed on Aug. 25, 2004 now abandoned, which claims priority to (1) PCT application Ser. No. PCT/US2004/005484, entitled "Sealed Surgical Access Device," filed on Feb. 25, 2004, (2) PCT application Ser. No. PCT/US2004/0054-87, entitled "Wound Retractor for Use in Hand-Assisted Laparoscopic Surgery," filed on Feb. 25, 2004, and (3) PCT application Ser. No. PCT/US2004/005361, entitled "Apparatus and Method for Illuminating a Peritoneal Cavity During Laparoscopic Surgery," filed on Feb. 24, 2004, all of which claim priority to provisional application Ser. No. 60/449,857, filed on Feb. 25, 2003, entitled "Hand-Assisted Laparoscopy Apparatus and Method," all of which are fully incorporated herein by reference in their entireties.

BACKGROUND OF THE INVENTION

1. Field of the Invention

This invention generally relates to surgical access systems that facilitate sealed access across a body wall and into a body cavity during a laparoscopic surgical procedure.

2. Discussion of the Relevant Art

During laparoscopic surgery, it is desirable to inflate the abdominal cavity in order to increase the volume of the working space. This is accomplished with an insufflation gas which must be maintained at a pressure sufficient to inflate the abdomen. Maintaining the pressure of the insufflation gas is difficult when it is also desirable to insert instrumentation through the abdominal wall. If a surgeon is interested in inserting his or her hand in a hand-assisted laparoscopic procedure, the maintenance of insufflation pressure is even more difficult. Currently, several devices exist that accomplish this surgical need although they suffer from drawbacks such as difficult placement and cumbersome use. For example, these hand-assisted devices require elaborate mechanisms such as inflatable cuffs and adhesives to seal around a surgeon's wrist or forearm to maintain the insufflation gases. As such, there is a need for a special seal formed around the wrist or forearm of a surgeon to prevent the escape of insufflation gases. Moreover, it is desirable that the wound be retracted, protected and fixed while maintaining the insufflation seal.

SUMMARY OF THE INVENTION

The invention is directed to a hand access system that provides hand access to a surgical area while maintaining pneumoperitoneum during laparoscopic surgery. The hand access system comprises a sheath retractor adapted to dilate a wound stretchable to a desired diameter, the sheath retractor includes a first ring being adapted for disposition interiorly of the wound, a second ring being adapted for disposition exteriorly of the wound, and a sheath being disposed in a generally cylindrical form between the first ring and the second ring and operable to exert a radial retraction force on the wound. The hand access system further comprises a detachable hand seal adapted to be attached and detached from the second ring of the sheath retractor. In particular, the hand seal can be detached from the sheath retractor to convert the hand access system from laparoscopic surgery to open surgery. In one aspect, the first ring, second ring and sheath are formed from an elastomeric material, and the hand seal is formed of a gel material and includes a slit providing an instrument seal in the presence of an instrument or hand and a zero seal in the absence of the instrument or hand. The gel material includes, for example, a thermoplastic base such as Kraton® and an oil. The resulting elastomer has excellent tear strength, elongation greater than 1,000 percent, a very low durometer or hardness, and biocompatibility. It is appreciated that the first ring has a first diameter and the second ring has a second diameter, and the first and second diameters are greater than the desired diameter of the wound.

In another aspect, the sheath retractor further comprises a third ring disposed circumferentially of the sheath and moveable between a plurality of positions between the first ring and the second ring, each of the positions being associated with a different retraction force, the third ring being adapted for disposition exteriorly of the wound. The sheath retractor may further comprise means for retaining the third ring at one of the plurality of positions in order to provide the desired radial retraction force associated with that position. The retaining means may comprise a fourth ring adapted to interlock with the third ring to fix the sheath at the desired position. The retaining means may include a wedge disposed between the third ring and the fourth ring.

In yet another aspect of the invention, the hand access system may further comprise an adapter having a first adapter cavity for releasably attaching to a ring of the retractor sheath and a second adapter cavity for releasably attaching to the hand seal. The first adapter cavity has a first diameter and the second adapter cavity has a second diameter.

In other aspects of the invention, the hand seal may include a cavity to receive the second ring of the sheath retractor, the hand seal may further comprise a latch on an inner diameter for latching the third ring, and the third ring may comprise at least a hook to latch the hand seal as the hand seal is attached to the sheath retractor. To facilitate sealing of the peritoneum, a conformable gasket may be provided that may be attached to the first ring or to the sheath of the sheath retractor, or the conformable gasket may float unattached to the sheath and interiorly of the wound.

In another aspect of the invention, the hand access system may comprise a detachable iris seal in place of the hand seal that is adapted to be attached and detached from the sheath retractor. The iris seal comprises a first iris ring, a second iris ring coaxially attached to the first iris ring, and a cylindrical elastic member connected to the first and second iris rings and having an opening. With this aspect, the first and second iris rings operate to rotate relative to one another in either direction to open or close the opening of the cylindrical elastic member. More specifically, the first and second iris rings may be rotated in opposite directions to create an airtight constriction in the middle of the elastic member. After rotation, at least one of the first and second iris rings may be de-rotated to loosen or enlarge the constriction of the elastic member.

Each of the iris rings may comprise a plurality of tracks to allow the iris rings to be relatively rotated at predetermined angles. In yet another aspect, the iris seal may further comprise a spring connecting the first and second iris rings to further facilitate a complete opening, a partial constriction or an airtight constriction of the opening of the elastic member. The spring operates to automatically pull and rotate the iris rings after de-rotation. In particular, as an object is withdrawn from the iris seal, the spring contracts and causes the sheath constriction to tighten automatically. The spring may be formed from an elastomeric material. It is appreciated that the amount the spring stretches and contracts is determined by the length of the spring. Each of the iris springs may comprise a hollow frame and a plurality of interlocking tracks. The interlocking tracks operate to encase the spring to prevent the spring from crossing into an instrument or hand passage area within the iris rings. The interlocking tracks also operate to open and close the seal at predetermined angles.

In another aspect of the invention, there is disclosed a surgical access device adapted for disposition relative to an incision in a patient comprising a valve including a plurality of overlapping sheets defining an access channel, and a ring having an inner diameter for holding the valve by fixing each of the overlapping sheets along a portion of the perimeter, the access channel extends into communication with the incision in the patient. With this aspect, each of the overlapping sheets includes a portion of the perimeter that is not fixed to the inner diameter of the ring. It is appreciated that the non-fixed portions provide open edges defining the access channel. In one aspect, the open edges slightly overlap for about 0.25" at the center of the ring. The hand access device may further comprise a septum seal formed at the proximal end and at the distal end of the ring, the septum seal having a hole formed at the center of the seal. It is further appreciated that the open edges of the non-fixed portions may have different shapes including at least one of a straight edge, concave, convex and a cross-configuration.

In yet another aspect of the invention, there is disclosed a surgical access device adapted for disposition relative to an incision in a patient comprising a plurality of septum layers each having a hole at the center of the septum layer and a first diameter, a ball sandwiched between the septum layers and having a second diameter greater than the first diameter, and a ring having an inner diameter for affixing the plurality of septum layers along the perimeter. In another aspect, a surgical access device facilitating a sealing relationship with an instrument or an arm of a surgeon extending through the device and into an incision in a patient is disclosed, the access device comprising a valve structure including a plurality of overlapping sheets defining an access channel, the valve in a first state forming a zero seal in the absence of the instrument or the arm of the surgeon extending through the valve structure, the valve in a second state forming an instrument seal in the presence of the instrument or the arm of the surgeon extending through the valve structure, and the access channel extends into communication with the incision in the patient.

These and other features of the invention will become more apparent with a discussion of the various embodiments in reference to the associated drawings.

DESCRIPTION OF THE DRAWINGS

The accompanying drawings, which are included in and constitute a part of this specification, illustrate the embodiments of the invention and, together with the description, explain the features and principles of the invention. In the drawings:

FIGS. 3A-3E illustrate axial perspective views and cross-sectional views of a hand access system in accordance with another embodiment of the invention including a one-way mechanism;

FIGS. 5A-5C illustrate an axial perspective view and cross-sectional views of a hand access system in accordance with another embodiment of the invention including a conformable gasket;

FIGS. 7A-7E illustrate the rotation of the iris seal rings of the invention to create an airtight constriction in the middle of the sheath;

DESCRIPTION OF THE INVENTION

Figure 1:
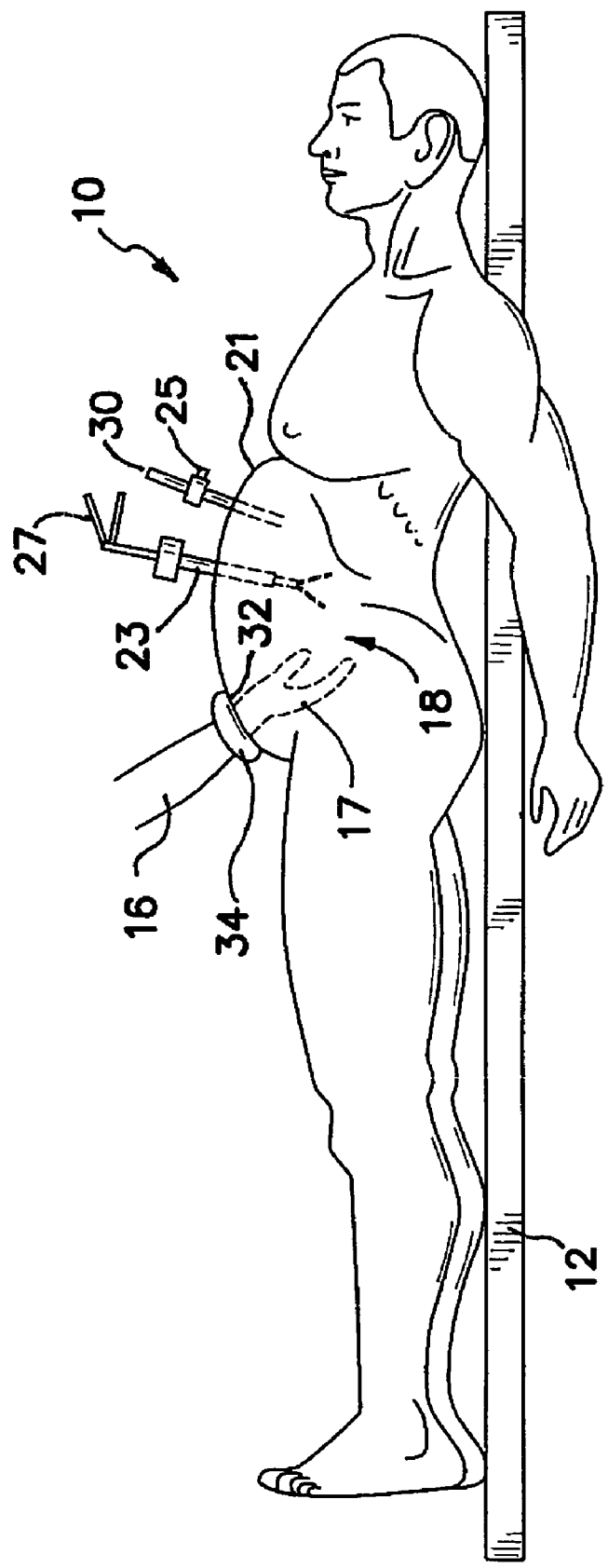
FIG. 1 is a perspective view showing a patient prone on an operating table with his abdomen insufflated and with instrument access provided by trocar and the access device of the present invention.

Referring to FIG. 1, there is shown a typical abdominal surgery on a patient 10 in a prone position on an operating table 12. FIG. 1 further illustrates a surgeon having an arm 16 and a hand 17 performing the surgery. In the illustrated example, the operative procedure is performed within an abdominal cavity 18 with instrument access provided through an abdominal wall 21. In this type of operation, commonly referred to as laparoscopic surgery, trocars 23 and 25 are commonly used to provide minimally invasive access through the abdominal wall 21 for instruments such as a grasper 27 and an endoscope 30. In addition, it is desirable that the surgeon be able to insert his/her hand 17 through the abdominal wall 21 and into the abdominal cavity 18. The insertion of the hand 17 provides the surgeon with direct access to various elements of the anatomy.

In order to accommodate the hand 17 and arm 16 of the surgeon, a small incision 32 is typically created in the abdominal wall 21. An access device 34 of the present invention can be provided to further facilitate this access by the hand 17 of the surgeon. Particularly in the case of laparoscopic surgery, it is advantageous to insufflate the abdominal cavity 18 with a gas, such as carbon dioxide, in order to elevate the abdominal wall 21 and thereby increase the volume of the working space within the cavity 18. Maintenance of this insufflation pressure, commonly referred to as pneumoperitoneum, is particularly difficult where access is desired across the abdominal wall 21, for example, through the trocars 23, 25, as well as the access device 34. For this reason, a substantial effort has been directed to providing such access devices with sealing characteristics both in the presence of instruments and in the absence of instruments, such as the grasper 27, scope 30 and hand 17.

Were it not for the desire to maintain the pneumoperitoneum, there would be no need for the trocars 23, 25 or the access device 34. That is, one would merely cut an incision in the abdominal wall 21 and insert the instrument directly through the incision. However, without appropriate valves or seals, the insufflation gases would merely escape through the incision 32. This would be particularly detrimental in the case of the incision 32 which must be sufficiently large to accept the hand 17 of the surgeon. Thus, the access device 34 operates to form with the incision 32 to provide an access or working channel, and to provide a valve or other sealing structure across the working channel in order to maintain the pneumoperitoneum.

Figure 2A:
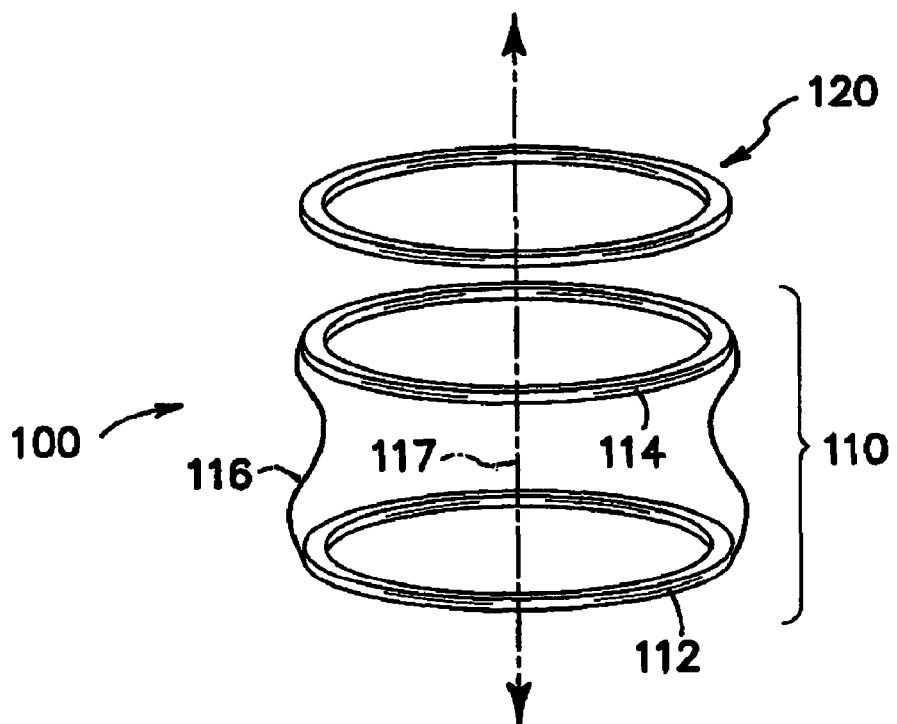
FIGS. 2A and 2B illustrate a perspective view and a cross-sectional view, respectively, of a hand access system in accordance with a first embodiment of the invention.
Figure 2B:
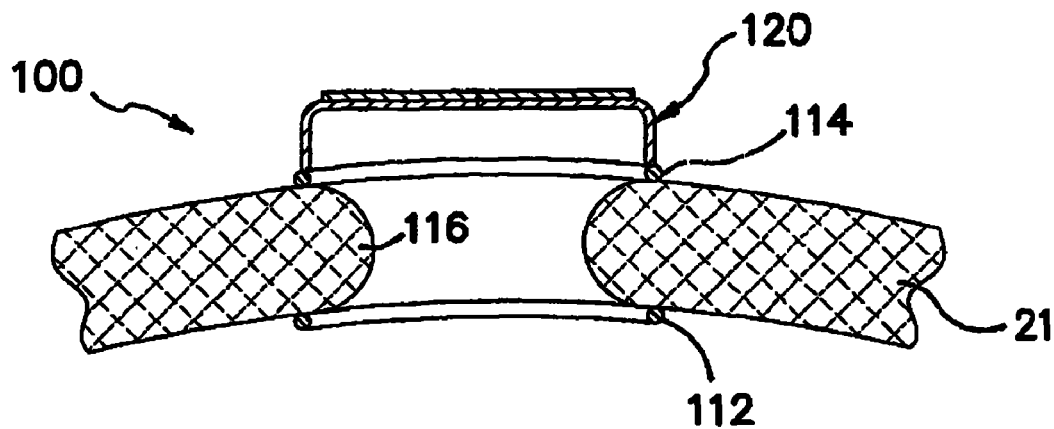

Referring to FIGS. 2A and 2B, there are shown a perspective view and a cross-sectional view, respectively, of a hand access system 100 of the invention. The hand access system 100 provides hand access to a surgical area such as the abdominal cavity 18 while maintaining pneumoperitoneum during laparoscopic surgery. The hand access system 100 comprises a sheath retractor 110 including a peritoneal ring 112, a proximal ring 114, and a sheath 116 extending along an axis 117 connecting the peritoneal ring 112 and the proximal ring 114. The sheath 116 has a generally cylindrical configuration that may be retracted to protect an incision within a body cavity such as the abdominal wall 21. The peritoneal ring 112 and proximal ring 114 are disposed in respective planes which extend radially of the axis 117. The hand access system 100 further comprises a detachable hand seal 120 that is operably attachable and detachable to the proximal ring 114 of the sheath retractor 110 as illustrated in FIG. 2B to permit insufflation. It is appreciated that the hand seal 120 can be separated from the sheath retractor 110 to allow removal of large organs or to provide open access to the abdominal cavity 18. Stated another way, the hand seal 120 can be removed at any time to allow conversion from laparoscopic surgery to open surgery.

It is further appreciated that wound retraction in accordance with the present invention allows a surgeon to easily locate the sheath retractor 110 and to provide a base for the hand seal 120. The sheath retractor 110 operates to remove the tissue pressure from the wrist during hand-assisted laparoscopic surgery. The sheath retractor 110 further protects tissue at the wound site, for example, from abrasion, bacteria or other contaminated organs, such as donor kidneys to be removed with minimal risk or damage. The sheath retractor 110 also opens the wound providing greater access to the operative site for instruments, such as the hand of the surgeon. In particular, the sheath protector 110 includes the sheath 116 having elastomeric properties that separate the two rings 112, 114. During surgery, the peritoneal ring 112 is placed interiorly of the abdominal wall 21 and the proximal ring 114 is placed exteriorly of the abdominal wall 21 and is then stretched beyond its natural state. The diameters of the rings 112, 114 are greater than that of the wound site so as to provide sufficient footing and tension between the rings 112, 114. This tension is created by the elastic material that has been stretched and retained at a distance greater than its natural state. It will be appreciated that in other embodiments, the sheath 116 can be formed of a non-elastic sheathing material. In a similar manner, the rings 112, 114 may be provided with a rigid configuration or alternatively may be formed of an elastomeric material.

Referring to FIGS. 3A and 3B, there are shown perspective views of a hand access system 100b where elements of structure similar to those previously described are designated by the same reference numeral followed by the lower case letter "b" in accordance with another embodiment of the invention. The sheath retractor 110b comprises a peritoneal ring 112b, a proximal ring 114b, a sheath 116b extending along an axis 117b connecting the peritoneal ring 112b and the proximal ring 114b, and a one-way mechanism 118b (a cylindrical plug) that is placed to extend above the incision. More specifically, the one-way mechanism 118b is placed between the peritoneal ring 112b and the proximal ring 114b. The hand access system 100b further comprises a "plug" hand seal 120b that is operably attached to the proximal ring 114b of the sheath retractor 110b. The hand seal 120b can be made of a soft gel material including a slit providing an instrument seal in the presence of an instrument or hand and a zero seal in the absence of an instrument or hand. The gel material includes, for example, a thermoplastic base such as Kraton® and an oil. The resulting elastomer has excellent tear strength, elongation greater than 1,000 percent, a very low durometer or hardness, and biocompatibility.

Figure 3C:
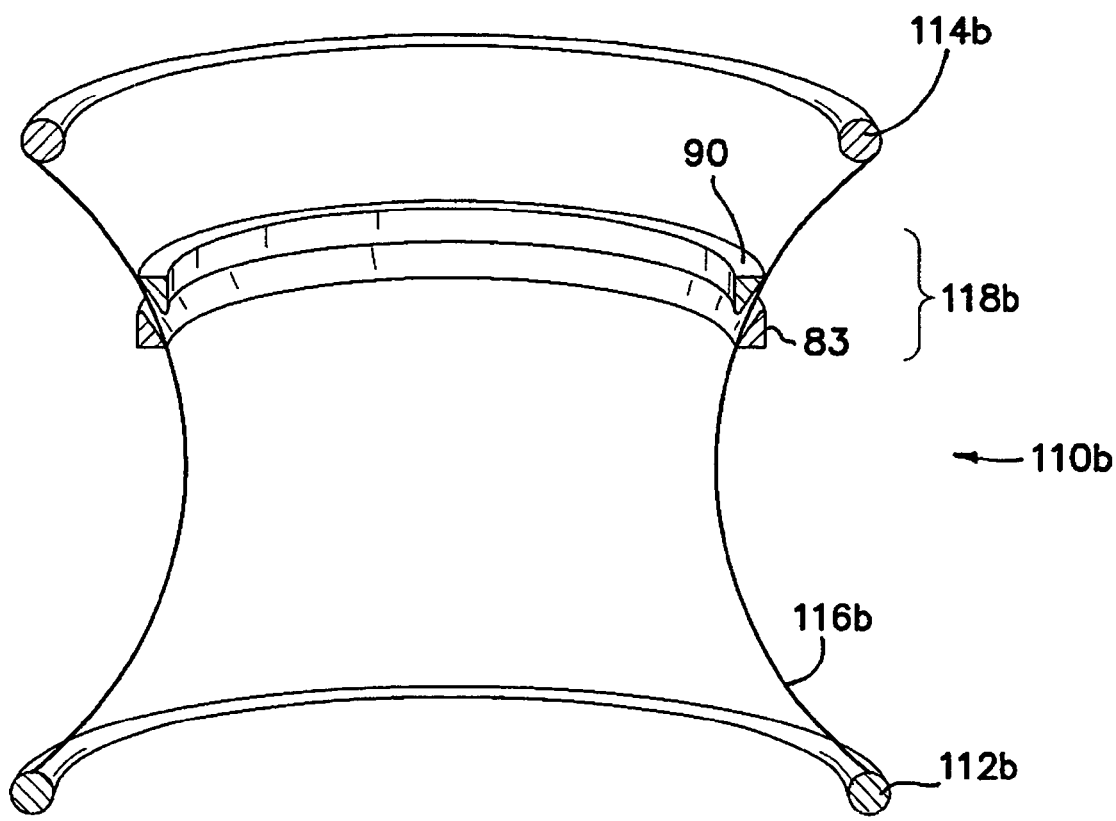
Figure 3D:
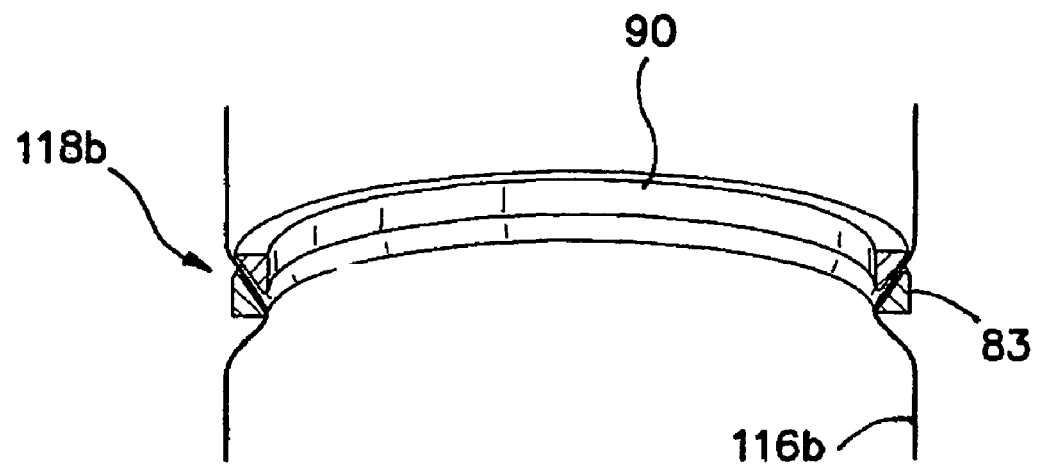
Figure 3E:
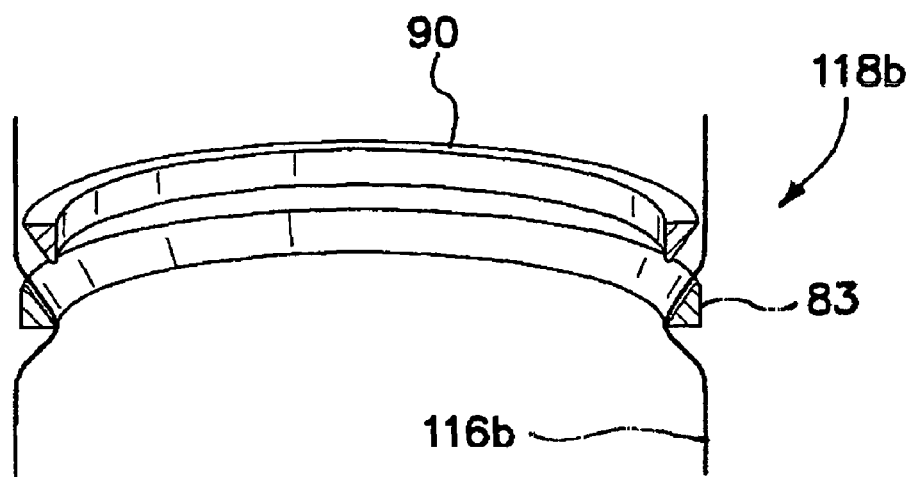

Referring to FIGS. 3C-3E, there are shown axial perspective views of an exemplary embodiment of the one-way mechanism 118b of the invention. Specifically, the one-way mechanism 118b comprises two complimentary interlocking rings 83 and 90. The proximal ring 114b can be disposed outwardly of the sheath 116b and the locking ring 90 can be disposed inwardly of the sheath 116b. These two rings 114b and 90 function to clamp the sheath 116b so that the ring 83 is maintained in a fixed position by the locking ring 90. The interlocking rings 83, 90 of FIG. 3C provide for simple operation of the sheath retractor 110b. These interlocking rings 83, 90 can be pushed down so that they rest on the outer surface of the abdominal wall 21. As the sheath 116b is drawn upwardly to achieve the proper degree of tension, it is easily moved between the interlocking rings 83, 90. However, any tendency of this sheath 116b to move back into the wound site will tighten the interlocking relationship of the rings 83, 90. Thus, the desired degree of tension is maintained on the sheath 116b until it is again pulled to release the locking ring 90 from the ring 83.

The one-way characteristics of the interlocking rings 83, 90 are further illustrated in the progressive views of FIGS. 3D and 3E. With reference to these figures, it can be seen that retraction is maintained by preventing the sheath 116b from pulling back into the wound by means of the one-way operation of the interlocking rings 83, 90. The sheath 116b slides easily through the interlocking rings 83, 90 in the upper direction, but is prevented from sliding through the rings 83, 90 in the downward direction. In order to disengage or separate the interlocking rings 83, 90, one needs only re-tension the sheath 116b by pulling it proximally thereby unlocking the rings 83 and 90. This enables the ring 83 to be removed from the sheath 116b in order to remove the retractor 116b from the wound site.

Figure 4A:
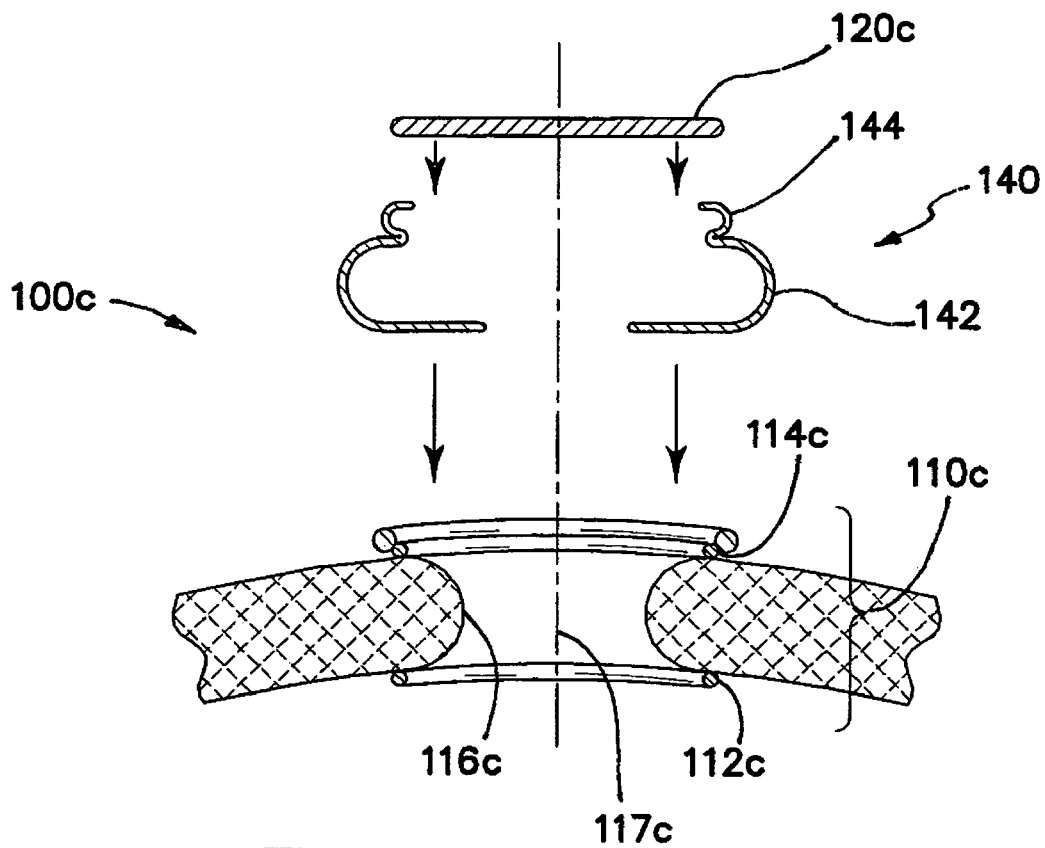
FIGS. 4A and 4B illustrate cross-sectional views of a hand access system in accordance with another embodiment of the invention including an adapter.
Figure 4B:
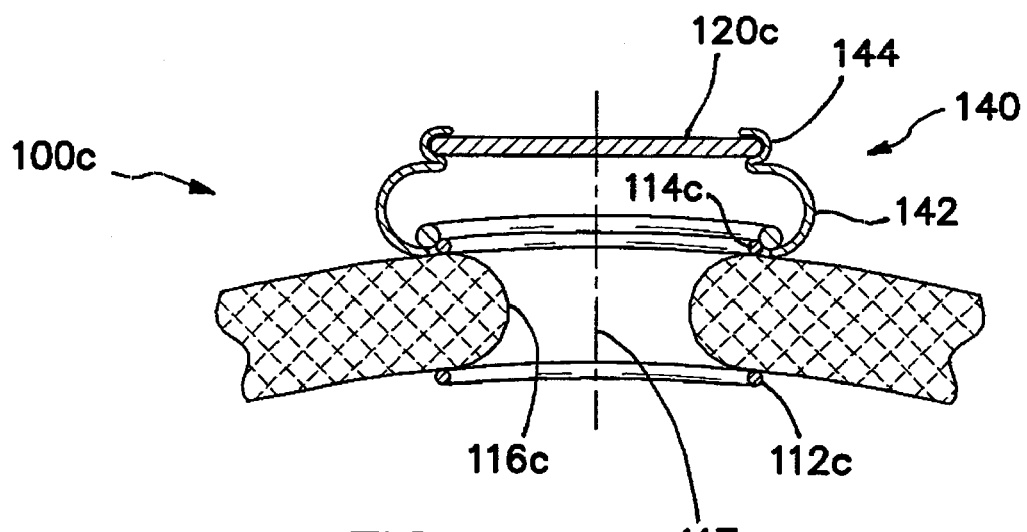

In another aspect of the invention, FIGS. 4A and 4B illustrate axial perspective views of a hand access system 100c comprising a sheath retractor 110c, an adapter 140 and a detachable hand seal 120c. The sheath retractor 110c includes a peritoneal ring 112c, a proximal ring 114c, and a sheath 116c extending along an axis 117c connecting the peritoneal ring 112c and the proximal ring 114c. The adapter 140 comprises a first or lower ring 142 for attaching to the proximal ring 114c of the sheath retractor 110c, and a second or upper ring 144 for attaching to the detachable hand seal 120c. FIG. 4B illustrates the hand access system 100c with the sheath retractor 110c, the adapter 140 and the hand seal 120c installed. More specifically, the adapter 140 is first attached to the proximal ring 114c of the sheath retractor 110c. In turn, the hand seal 120c may be attached and detached from the upper ring 144 of the adapter 140 as needed.

It is appreciated that the proximal ring 114c may further include a movable ring, which together with the proximal ring 114c, may be used to press down on the adapter 140 against the abdomen, for example, to secure it and form an airtight connection. It is further appreciated that the upper ring 144 may have a diameter that is great than, equal to or less than the diameter of the lower ring 142. In another aspect of the invention, the adapter 140 may further comprise grooves to snap in a self-closing iris seal to gain pneumoperitoneum.

Figure 5A:
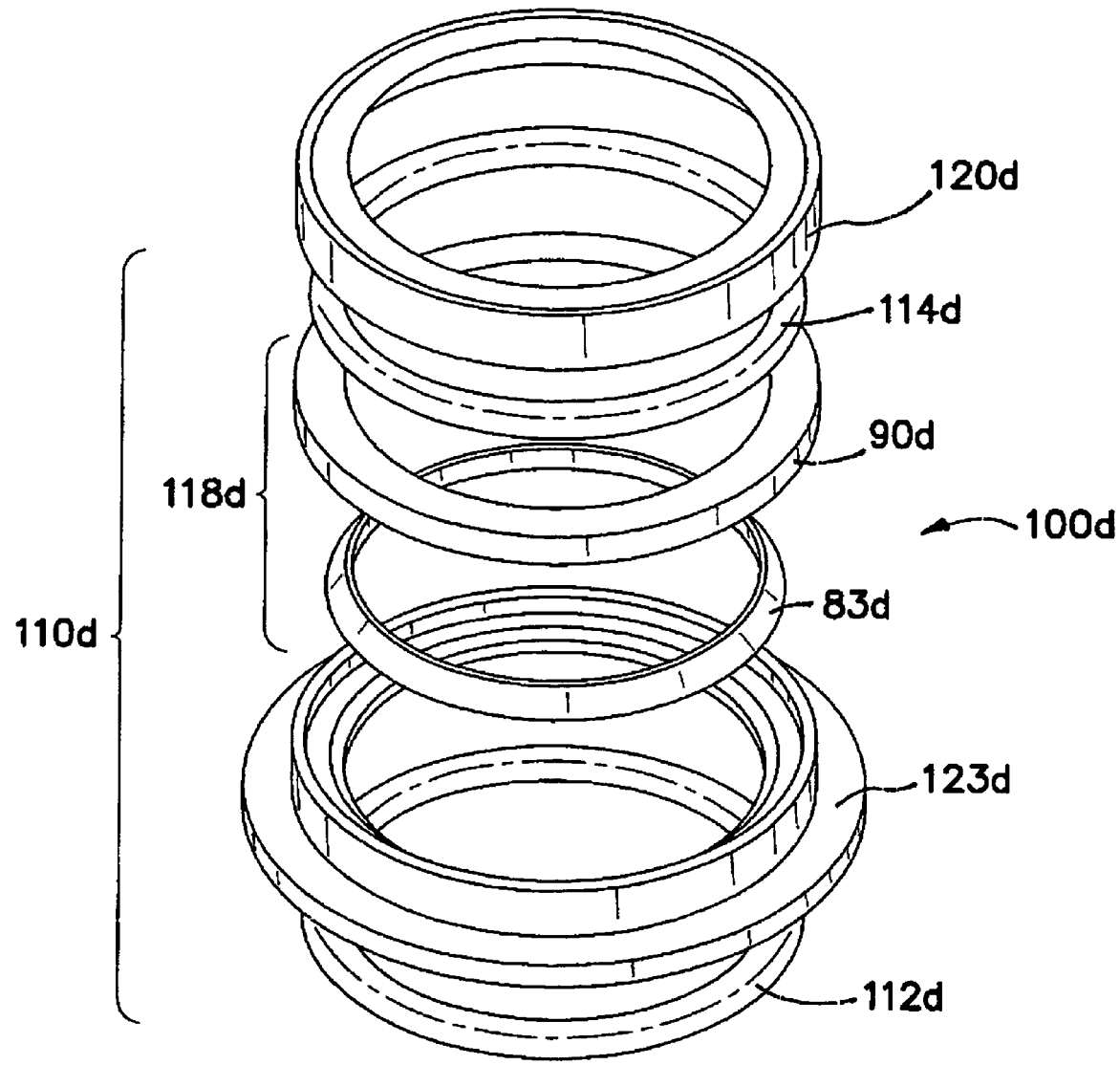
Figure 5B:
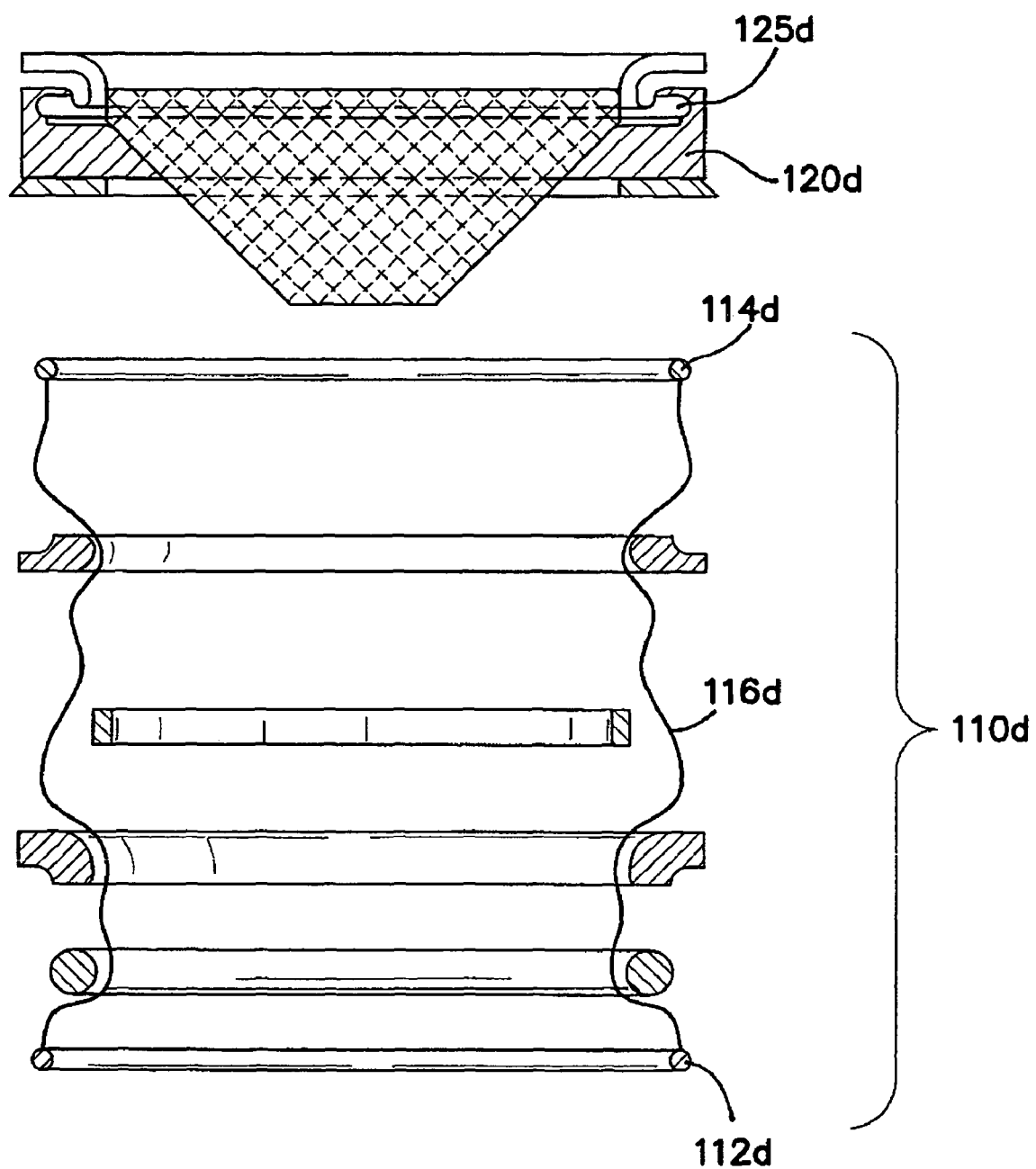

FIGS. 5A-5C illustrate perspective and cross-sectional views of a hand access system 100d in accordance with yet another embodiment of the invention where elements of structure similar to those previously described are designated by the same reference numeral followed by the lower case letter "d". The hand access system 100d comprises a sheath retractor 110d and a hand seal 120d operably attached to the sheath retractor 110d. The sheath retractor 110d includes a peritoneal ring 112d, a proximal ring 114d, a sheath (not shown) connecting the peritoneal ring 112d and the proximal ring 114d, and a one-way mechanism 118d comprising a plurality of interlocking rings 83d, 90d. The hand seal 120d operably attaches to the proximal ring 114d of the sheath retractor 110d. The hand seal 120d may be formed of a soft gel material and includes a small slit to allow passage of a hand or a surgical instrument during surgery. Referring to FIG. 5B, there is shown a cross-sectional view of the hand seal 120d having a cavity 125d inside the gel to receive the proximal ring 114d of the sheath retractor 110d. Referring to FIG. 5C, the hand seal 120d may further comprise a latch 121d on an inner diameter for latching the one-way mechanism 118d. The access sheath material may be placed inside or outside of the hand seal 120d after attachment of the hand seal 120d and the seal retractor 110d.

In another aspect, the one-way mechanism 118d may include hooks to latch the hand seal 120d as the seal 120d is pressed down on the open end of the sheath. As explained above, the hand seal 120d includes a small slit in the gel that will not allow air to pass with the absence of an instrument or hand, but the slit will stretch and the gel will compress to allow objects to pass through with little loss of pneumoperitoneum. Compression of the gel onto the proximal ring 114d of the sheath retractor 110d creates an airtight connection. The sheath retractor 110d, as illustrated in FIG. 5A, may further include a conformable gasket 123d to facilitate sealing of the peritoneum. The conformable gasket 123d on the peritoneum ensures an airtight seal inside the incision as opposed to outside the incision. The gasket 123d can be attached to the peritoneal ring 112d or the sheath 116d, or it can float unattached to the sheath. The floating gasket 123d is less likely to crease or bunch (a path for air leaks) as the abdominal wall 21, sheath 116d and peritoneal ring 112d distort as the sheath 116d is pulled up into the incision. Without the need for sealing externally on the skin surface, the conformable gasket 123d is not susceptible to air leaks for irregularities on the skin, such as scars or folds. Furthermore, the conformable gasket 123d protects the abdominal wall 21 from potential traumatic pressure or abrasion by the peritoneal ring 112d.

In all of the above embodiments of the invention, the ability to attach and detach the hand seal from the sheath retractor allows larger objects to pass unfettered through the incision.

In addition, the invention is easy to use, it provides increased comfort for the surgeon, and is less traumatic to tissue being passed through the incision. For example, the latching or interlocking feature of the hand seal and the adapter with the sheath retractor makes it fast and simple to use compared to other methods that may involve inflatable cuffs or adhesives. Adhesives often require time to cure and inflation with pumps also creates delay.

Figure 6:
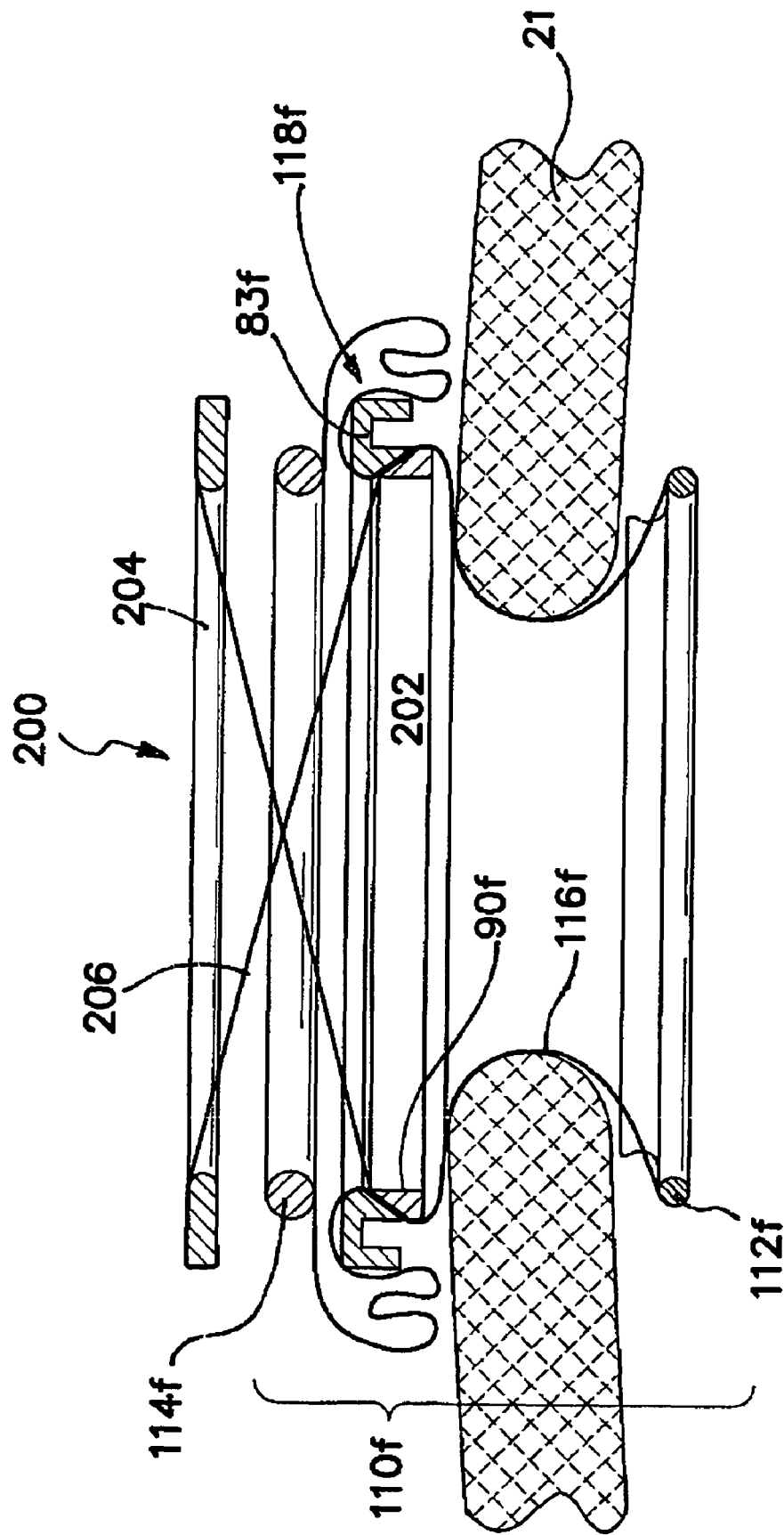
FIG. 6 illustrates a cross-sectional view of a hand access system in accordance with another embodiment of the invention including an iris seal.
Figure 7D:
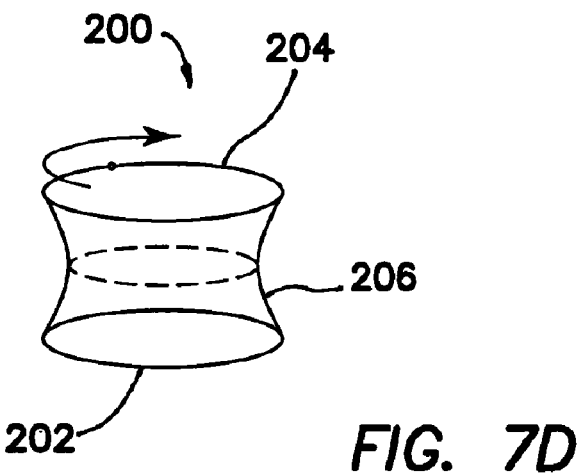
Figure 7D:
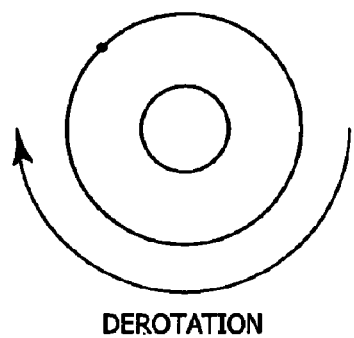
Figure 7E:
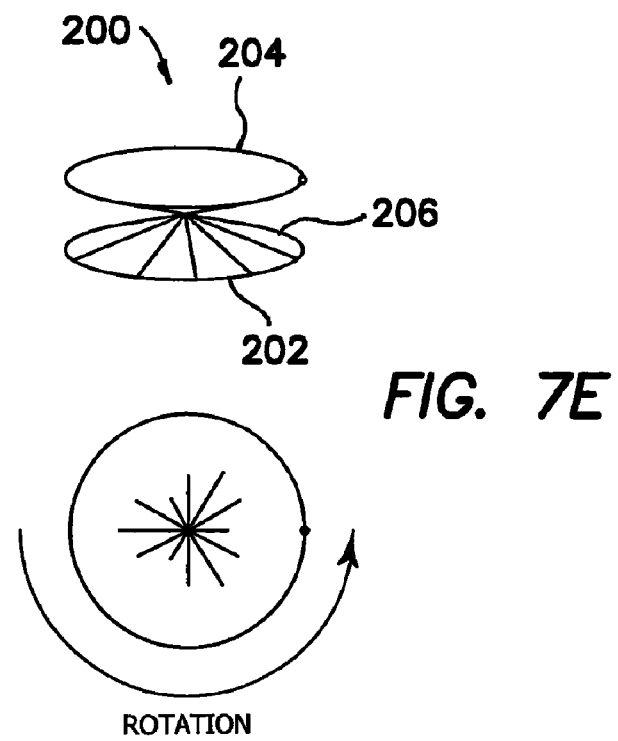
Figure 7E:
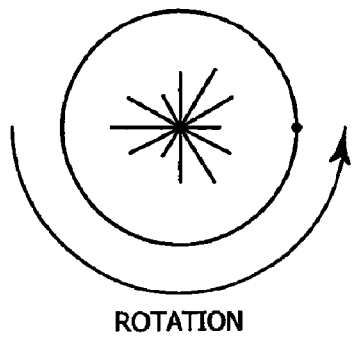

In another aspect of the invention, the hand access system may comprise a sheath retractor and an iris seal directly connected to the sheath retractor to form a continuous, seamless sheath. Referring to FIG. 6, there is shown a hand access system in accordance with another embodiment of the invention including an iris seal 200. The iris seal 200 comprises a first ring 202, a second ring 204 coaxially attachable to the first ring 202, and a cylindrical elastic member 206 connected to the first and second rings 202, 204 and having an opening. The first and second rings 202, 204 operate to rotate relative to one another in either direction to open or close the opening of the cylindrical elastic member 206. In particular, the seal 200 operates like the iris aperture of a camera, except that the iris seal 200 is made of a thin film sheath or elastic member 206. A ring 202, 204 is attached to each end of the sheath or elastic sheath 206. Referring to FIGS. 7A-7C, the rings 202, 204 are rotated in opposite directions to create an airtight construction in the middle of the sheath or elastic member 206. The constriction is maintained as long as the rotation is not undone (termed de-rotation). The sheath or elastic member 206 can be made of an elastic material, which allows objects small in diameter relative to the rings 202, 204 to pass easily through the constriction without the need for de-rotation. However, objects with large diameters may require de-rotation to loosen or enlarge the constriction in the sheath as illustrated in FIG. 7D. Once an object is withdrawn, the rings 202, 204 must rotate back to create the airtight construction as illustrated in FIG. 7E. In another aspect, the rings 202, 204 may include a plurality of tracks 207 such that they may be relatively rotated to open or close the opening at predetermined angles as further discussed below and illustrated in FIG. 10. More specifically, the sectional area of the opening changes in response to the predetermined angle rotation of the rings.

Referring back to FIG. 6 the iris seal 200 may be attached to a sheath retractor 110f having a peritoneal ring 112f, a proximal ring 114f, a sheath 116f connecting the peritoneal ring 112f and the proximal ring 114f, and a one-way mechanism 118f (comprising a plurality of interlocking rings 83f, 90f). A feature of the iris seal 200 is its constriction can be dilated as wide as the retracted incision and, as such, it may not be necessary for it to be detached from the sheath retractor 110f. In this case, the iris seal 200 can be made a permanent part of one of the interlocking rings of the one-way mechanism 118f. Thus, the self-closing iris seal 200 and sheath retractor 110f combinations allows pneumoperitoneum to be regained more quickly without having to detach and reattach a seal as with previous methods. In another aspect, an iris seal can be easily removed when constructed as part of a two-ring design in the form of a wedge clamp similar to that shown in FIGS. 3C-3E. Pulling up on a sheath pushes or un-wedges the seal out of the sheath retractor.

Figure 8A:
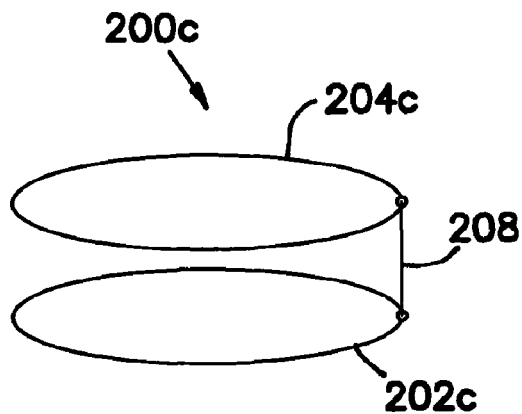
FIGS. 8A-8C illustrate side views of another embodiment of the iris seal including a spring connecting the two rings.
Figure 8B:
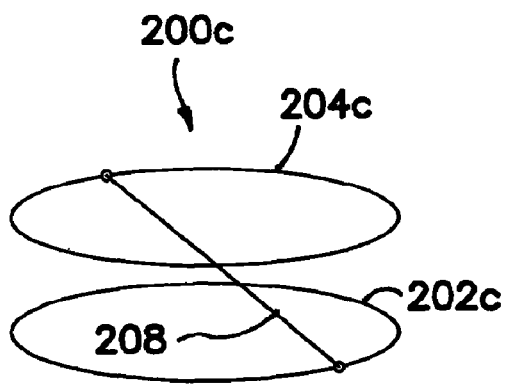
Figure 8C:
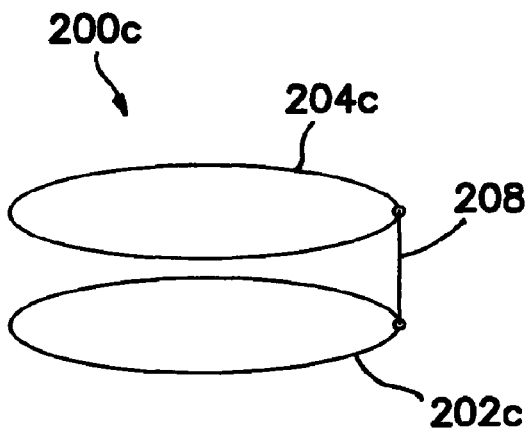
Figure 9:
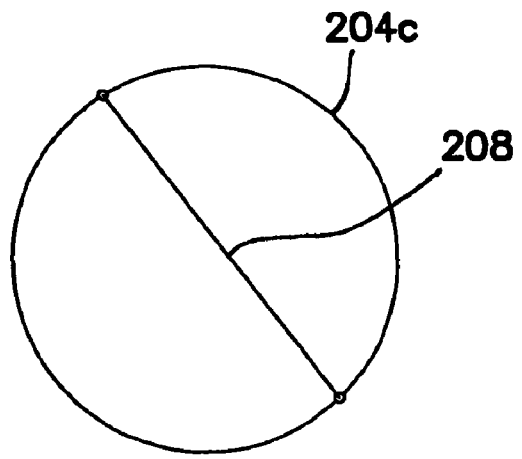
FIG. 9 illustrates a top view of FIG. 8B.

It is appreciated that other hand seals can be used and interchanged as contemplated by the concept of the invention. For example, the iris seal of the invention may further include a spring 208 connecting the first and second rings 202, 204 to further facilitate the opening and closing of the opening of the cylindrical elastic member 206. More particularly, one or more springs 208 may be used to connect the first and second rings 202, 204 to provide a complete opening, a partial constriction or an airtight constriction of the iris seal. Referring to FIGS. 8A-8C, there are shown perspective views of the iris seal 200c of the invention further comprising the spring 208 connecting the first and second rings 202c, 204c. FIG. 9 is a top view of the iris seal 200c of FIG. 8B.

Figure 10:
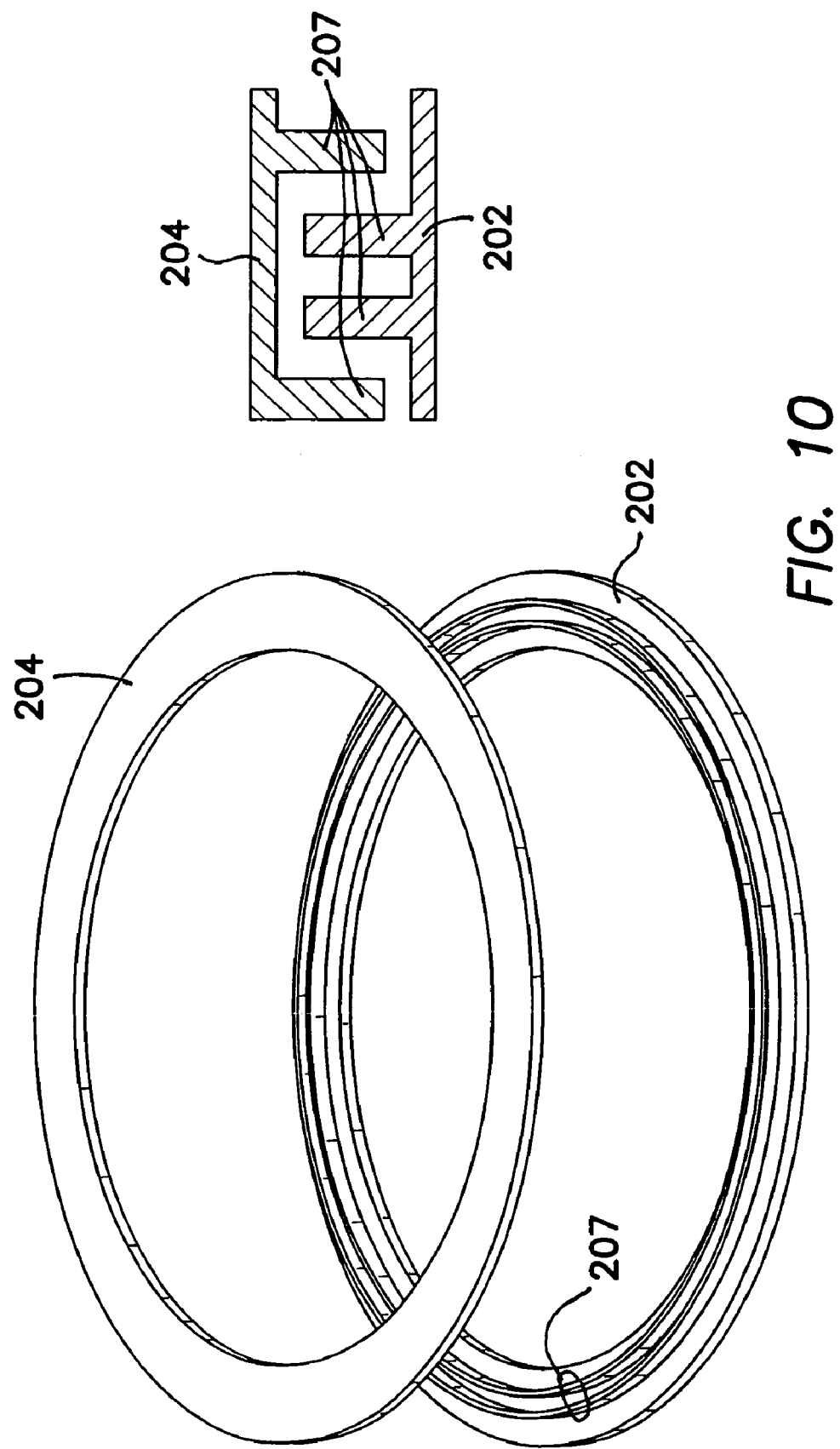
FIGS. 10 and 11 illustrate perspective and top views of rings of an iris seal having interlocking tracks in accordance with another embodiment of the invention.
Figure 11A:
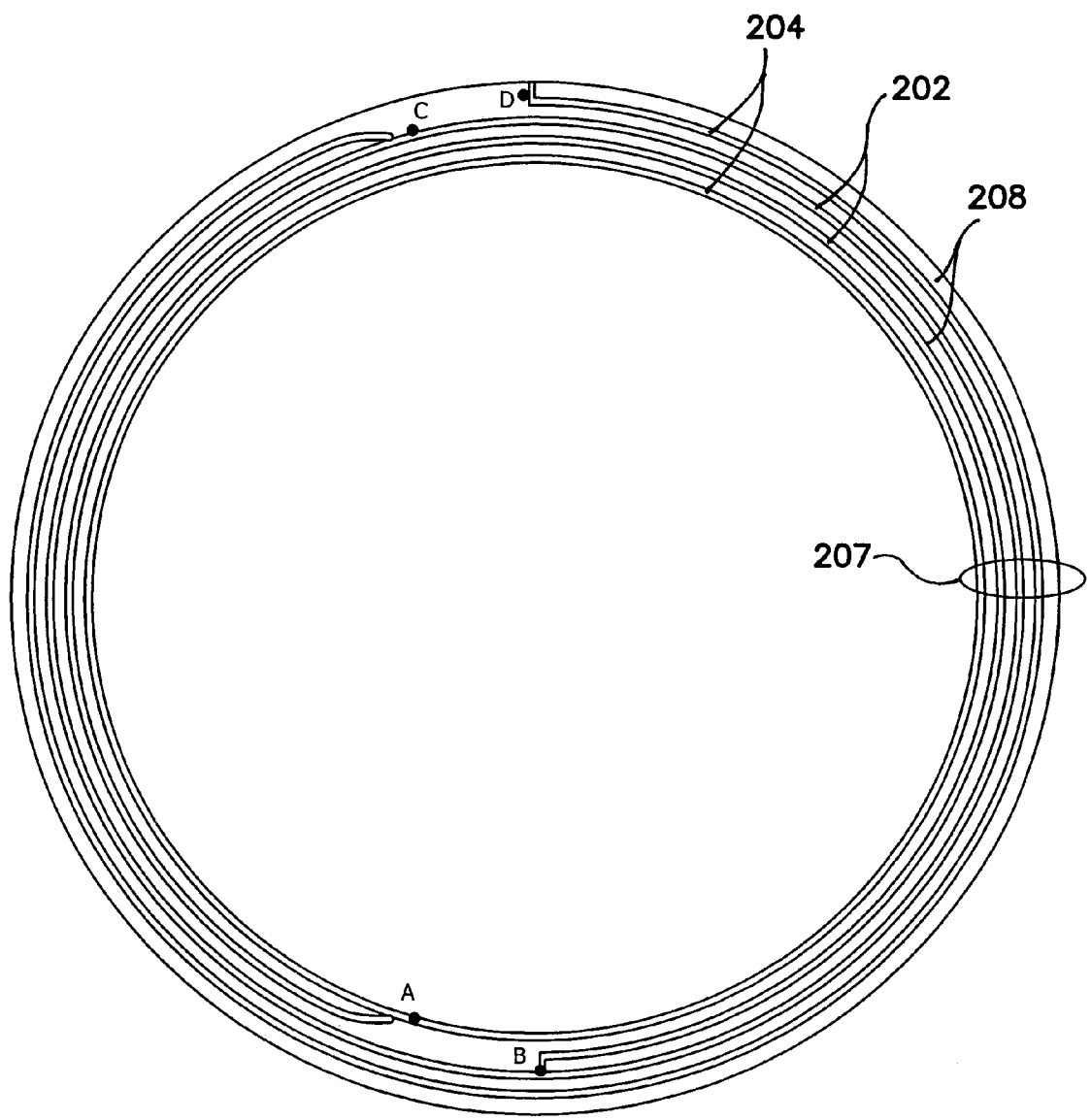
Figure 11B:
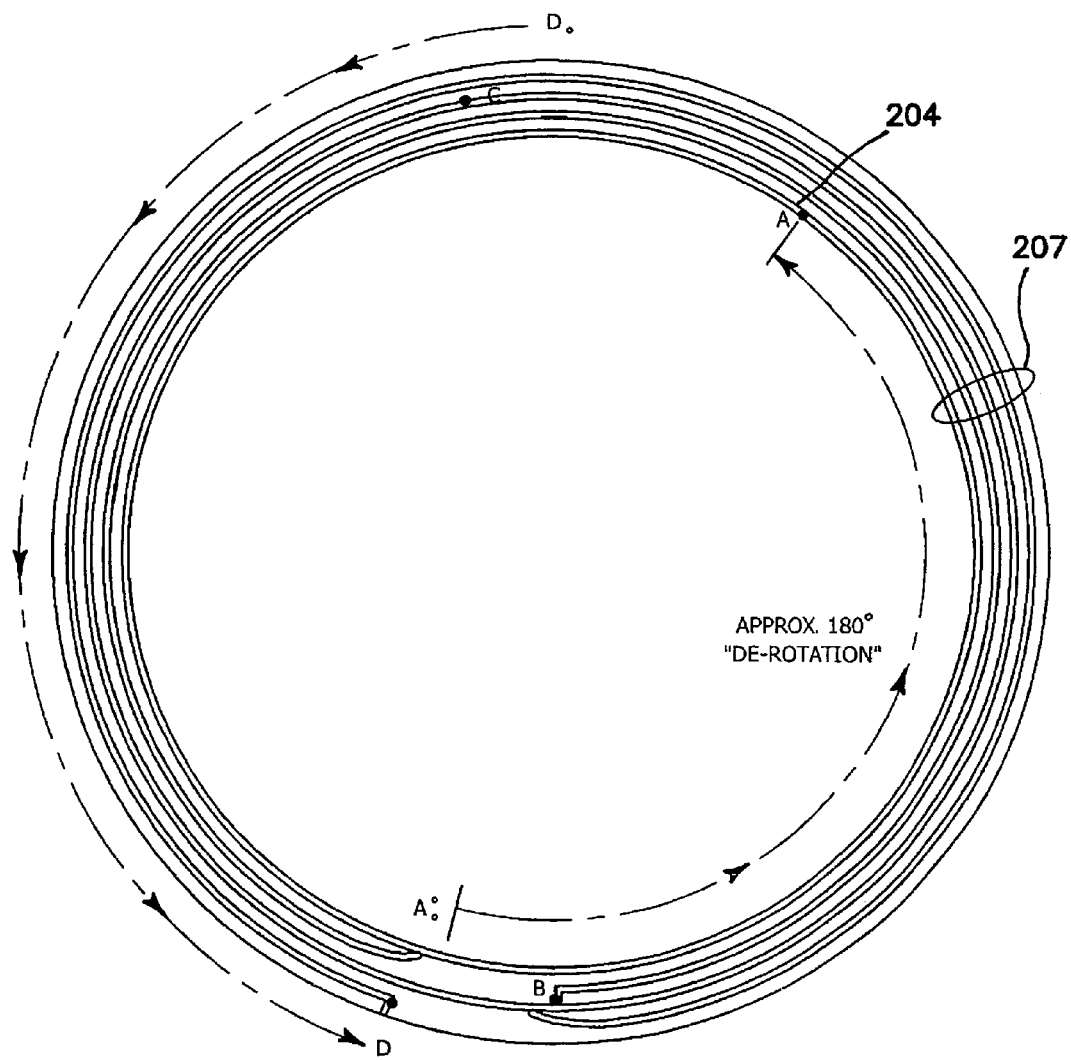

As illustrated in FIGS. 8 and 9, as the rings 202c, 204c are rotated relative to one another, the spring 208 expands and contracts causing opening and constriction of the seal. More specifically, the spring 208 can be used to pull and rotate the rings 202c, 204c automatically after de-rotation, for example. The ends of the spring 208 are connected to the rings 202c, 204c in a manner such that de-rotation causes the spring 208 to stretch as illustrated in FIGS. 8A and 8B. Afterwards, the spring 208 contracts and causes the sheath constriction to tighten automatically as large objects are withdrawn (FIG. 8C). The amount the spring 208 stretches and contracts is determined by the length of the spring 208—typically larger objects require longer springs. Longer springs, however, may crossover the area within the rings 202c, 204c and interfere with the passage of objects as illustrated in FIG. 9. To limit interference and to accommodate large objects, longer springs can be housed partially within a series of interlocking tracks 207 of hollow frame rings 202d, 204d as illustrated in FIGS. 10 and 11. In particular, the interlocking tracks 207 on the rings can encase longer springs so they do not cross into the passage area. The interlocking tracks 207 also operate to open and close the seal at predetermined angles. FIG. 11A illustrates an axial cross-sectional view of the seal with the springs contracted and the iris closed, and FIG. 11B illustrates an axial cross-sectional view of the seal with the springs expanded and the iris opened.

An advantage of rotational adjustment, versus fixed rings, is that a wider range of object sizes can easily pass through the iris seal. A self-closing mechanism of the invention has the advantage of hands-free adjustment. In comparison to other self-closing methods that involve gears and springs that are connected to stationary components external to the iris seal, the spring(s) of the present invention are connected to and contained within the rings, which are integral to the iris seal. With the self-closing mechanism built in, the iris seal is portable and can be more easily adapted to a wide range of access ports, wound retractors and the like.

Figure 12:
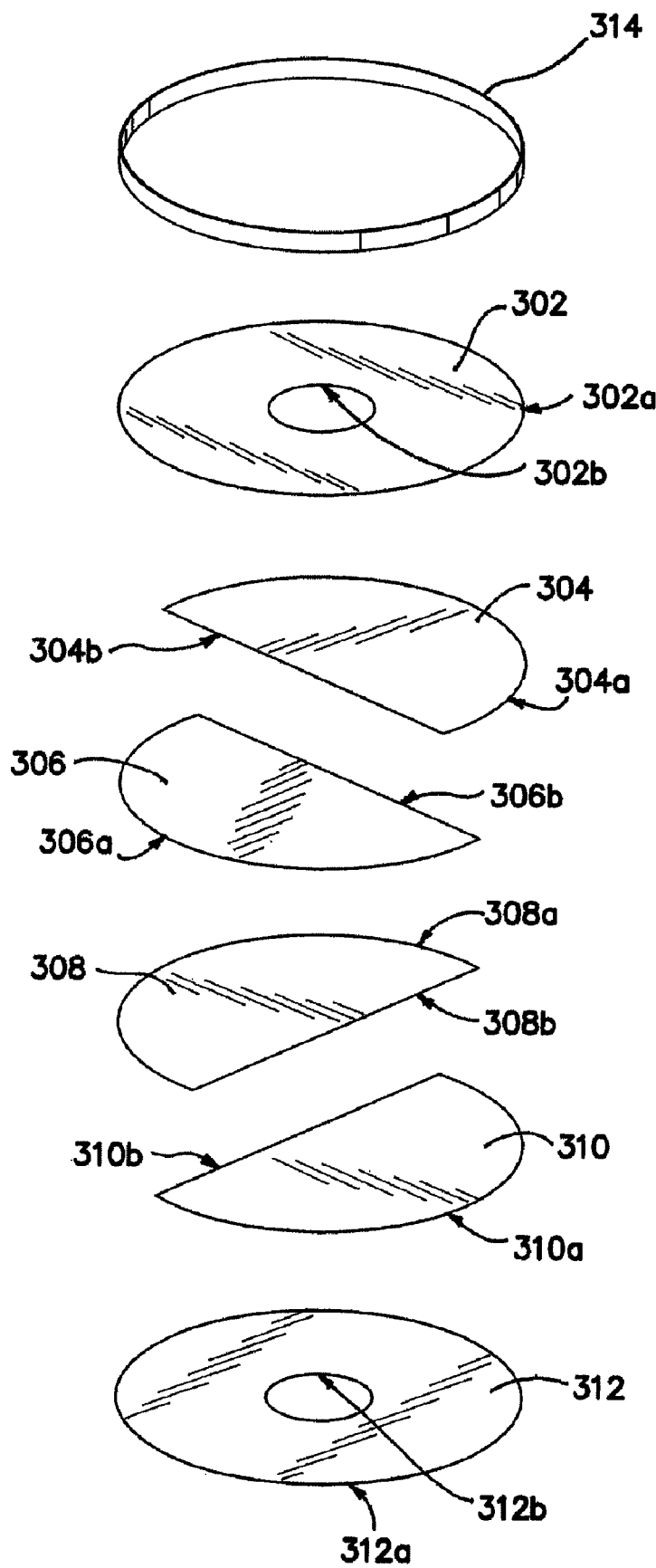
FIG. 12 illustrates a perspective view of a hand-assisted laparoscopic seal formed by overlapping sheets of elastomeric material in accordance with another embodiment of the invention.

In another aspect of the invention, a hand-assisted laparoscopy seal 300 is formed by overlapping several sheets 302, 304, 306, 308, 310, 312 of elastomeric material as illustrated, for example, in FIG. 12. Each of these sheets 302, 304, 306, 308, 310, 312 is fixed along a portion of its perimeter to the circumference of a semi-rigid or rigid ring 314. As a result, each of the sheets 302-312 has at least a portion 302a, 304a, 306a, 308a, 310a, 312a of its perimeter fixed to the ring 314 and a portion 302b, 304b, 306b, 308b, 310b, 312b not fixed to the ring 314. These non-fixed portions 302b-312b provide open edges within the area of the ring 314. The sheets 302-312 are laid on top of one another and are rotated so that open edges extend along different planes. These open edges slightly overlap, such as approximately one-quarter inch, at the center of the ring to prevent leakage of the insufflation gas. During operation, an instrument or hand of the surgeon is introduced through the center of the ring 314 forcing the open edges to part, but also causing the open edges to form a sealing structure around the forearm or wrist.

Figure 13:
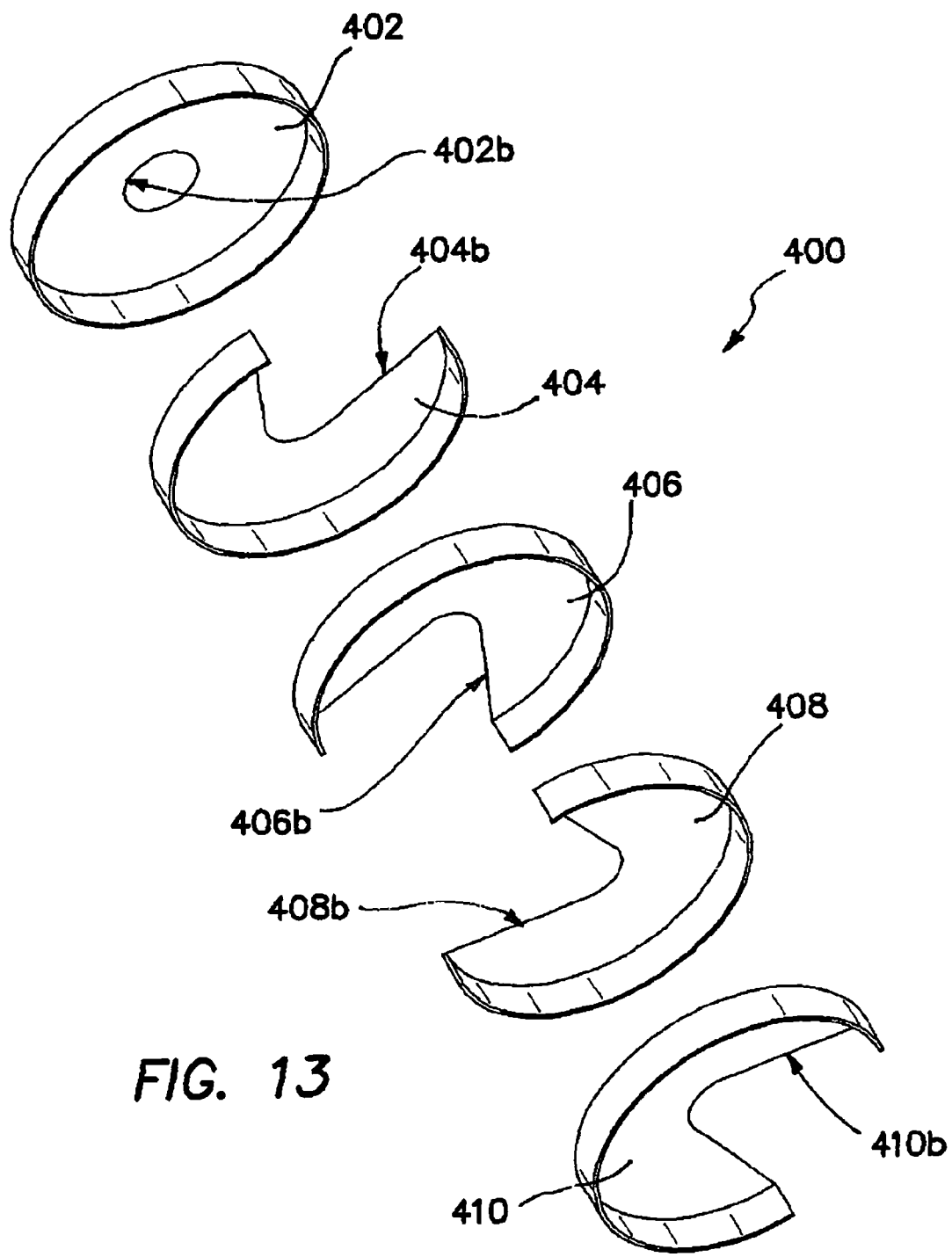
FIG. 13 illustrates a perspective view of a hand-assisted laparoscopic seal formed by differently shaped overlapping sheets of elastomeric material in accordance with another embodiment of the invention.

It is appreciated that in the above aspect, the overlapping sheets 302, 312 may comprise two septum sheets having their full perimeters fixed to the ring and a hole formed at the center of the septum sheets. Referring to FIG. 13, there is shown another aspect of the invention where the open edges 404b, 406b, 408b, 410b have different shapes, which when laid on top of one another, tend to form overlapping sections of a circle. It is appreciated that the concept of the invention contemplates any number of overlapping sheets of any material and of any shape. In one simple embodiment, for example, the invention contemplates two semi-circular sheets having slightly straight overlapping edges.

Figure 14:
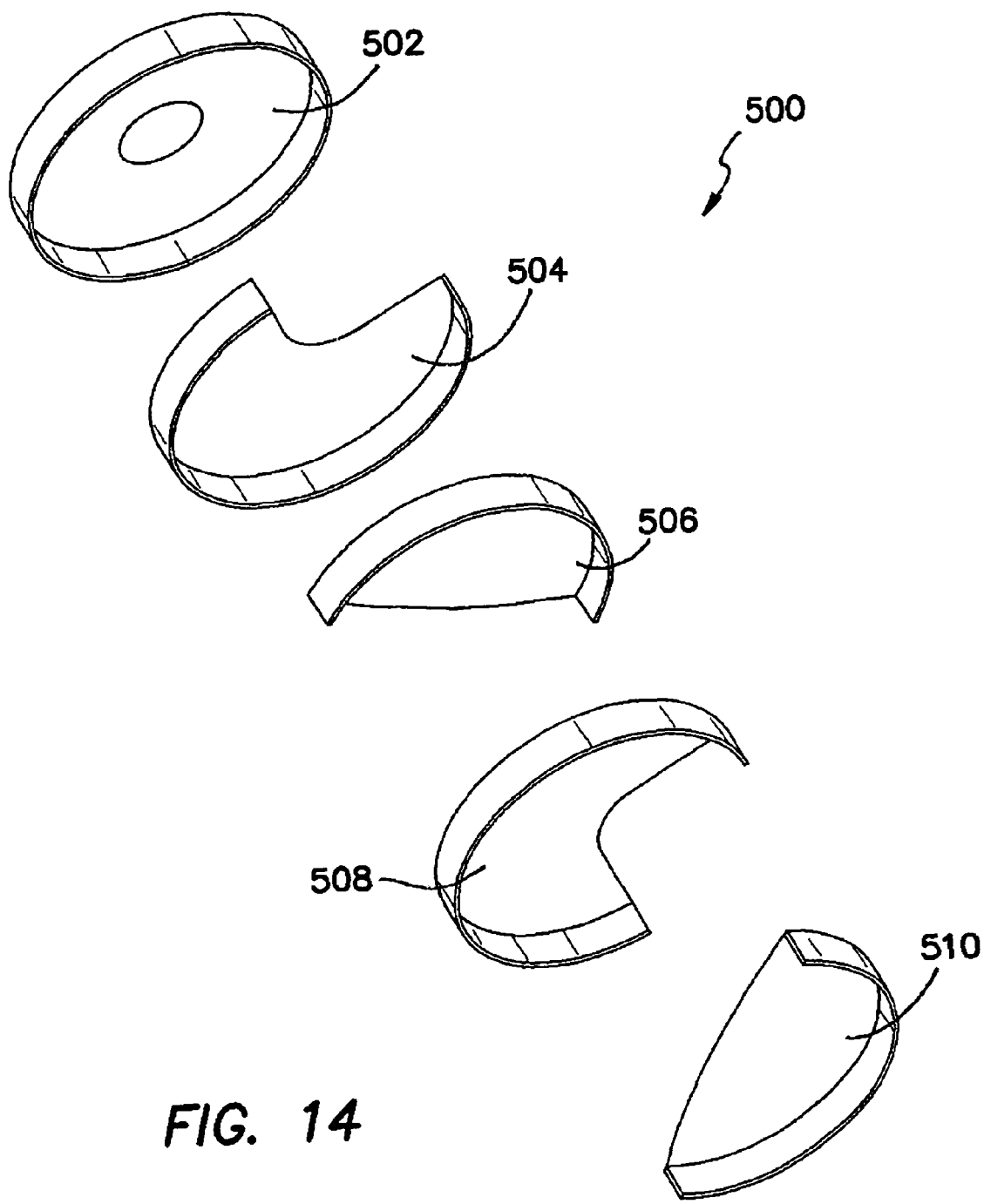
FIGS. 14 and 15 illustrate perspective views of a hand-assisted laparoscopic seal formed by overlapping sheets of elastomeric material having concave and convex configurations.
Figure 15:
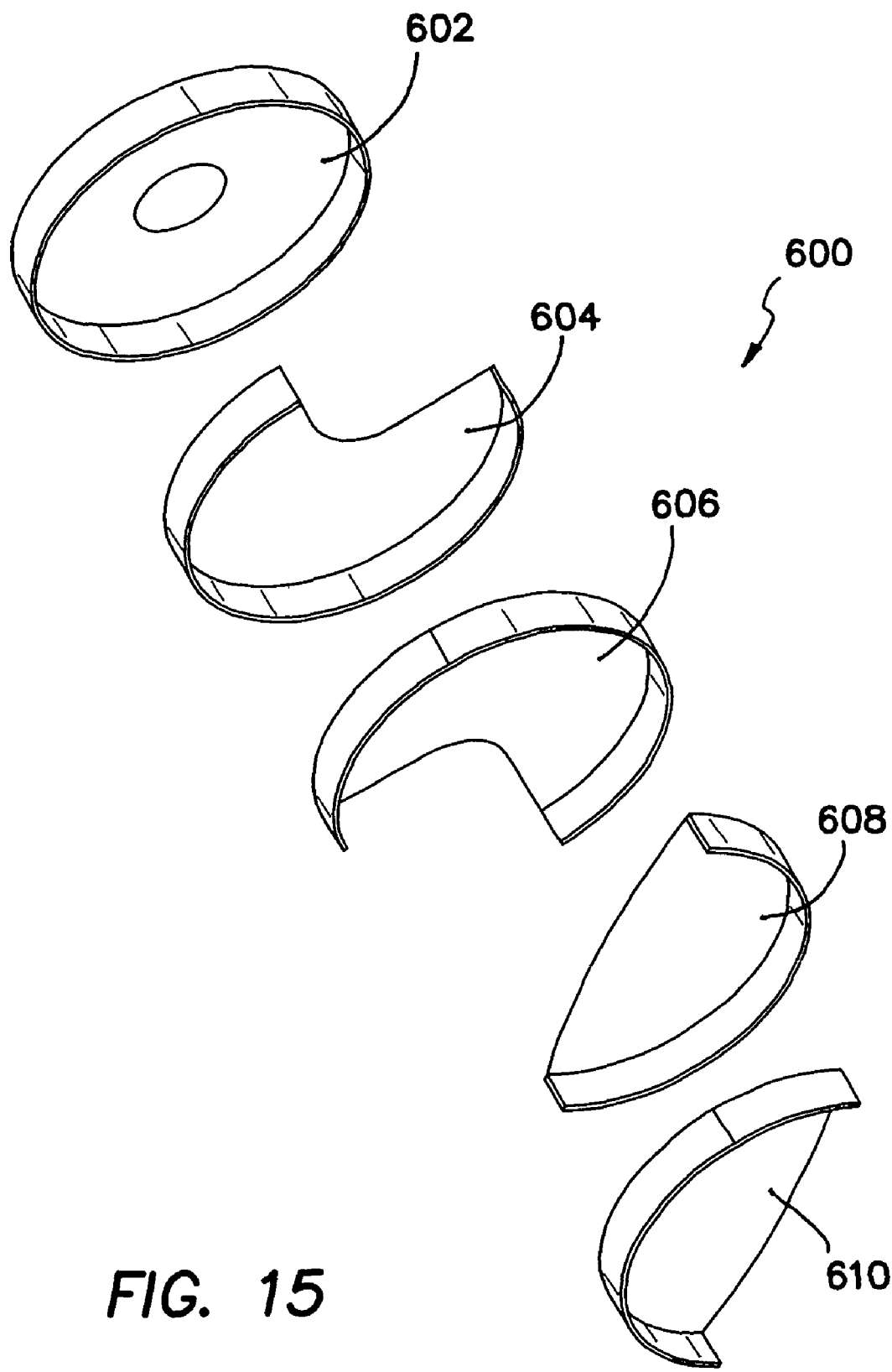
Figure 16:
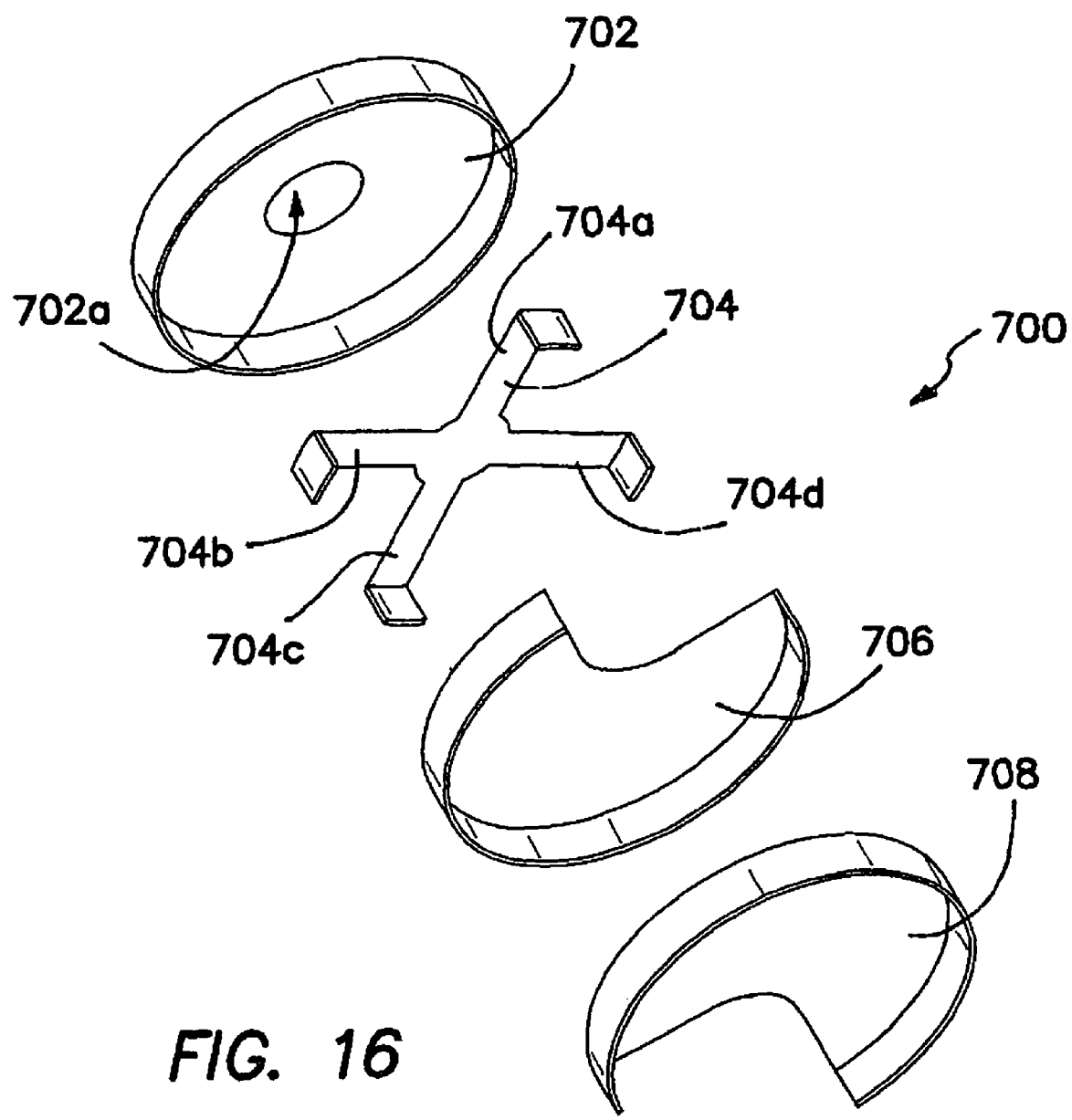
FIG. 16 illustrates a perspective view of a hand-assisted laparoscopic seal formed by overlapping sheets of elastomeric material including a central patch supported by spokes in accordance with another embodiment of the invention.
Figure 17:
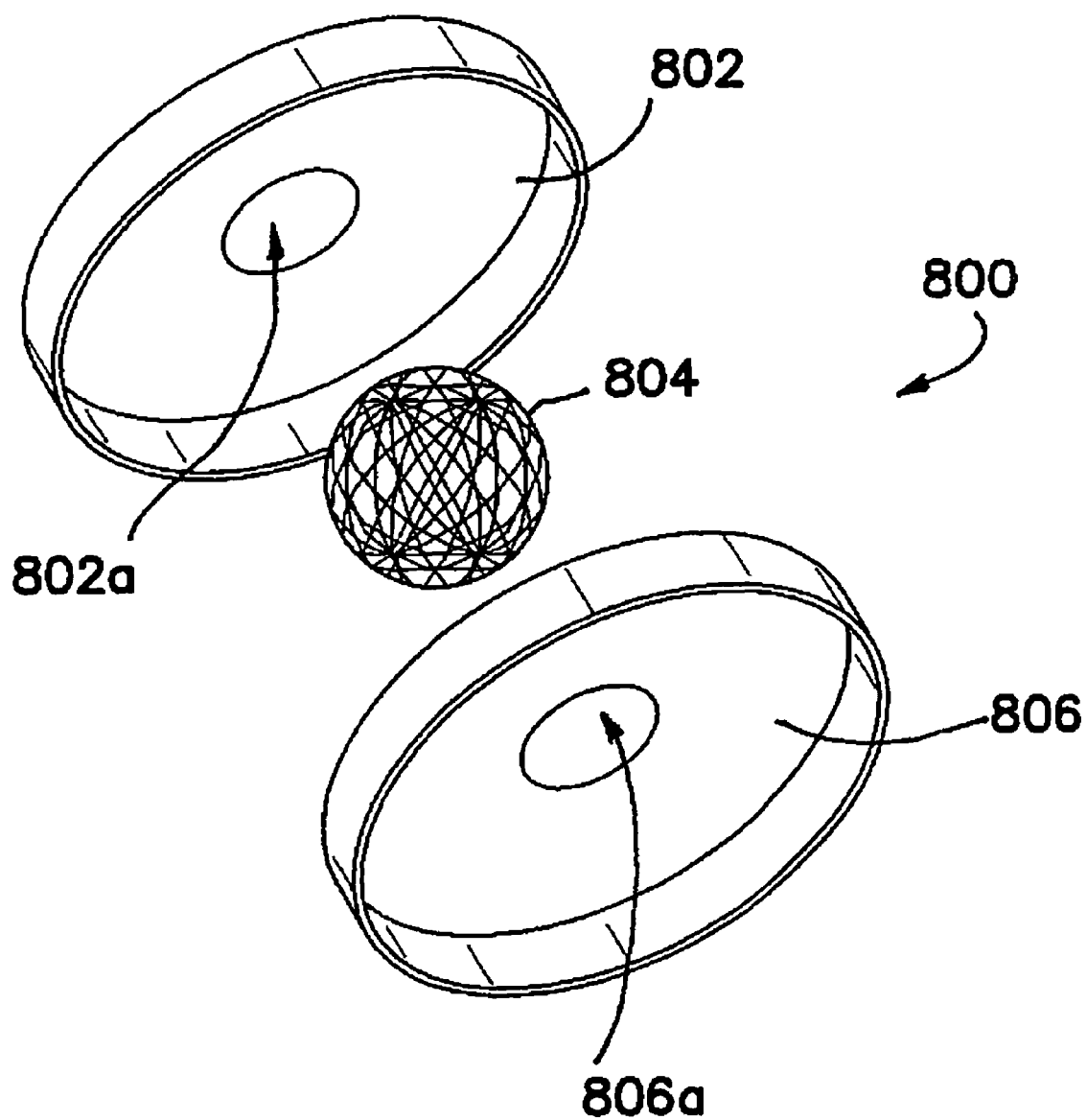
FIG. 17 illustrates a perspective view of a hand-assisted laparoscopic seal formed by two septum layers sandwiching a ball in accordance with another embodiment of the invention.

In another aspect, FIGS. 14 and 15 show how the open edges can be provided with concave or convex configurations. The sheets or layers having convex open edges 506, 510, 608, 610 tend to flex more while the sheets or layers having concave edges 504, 508, 604, 606 tend to give more support. The septum sheets or layers 502, 602 provide the most support. Other shapes can be used for the layers as illustrated in the embodiment of FIG. 16 where one of the layers includes a central patch 704 supported by spokes 704a, 704b, 704c, 704d which extend to the ring. The central patch 704 is large enough to cover the hole 702a in the septum layer 702. In the embodiment of FIG. 17, two septum layers 802, 806 sandwich a ball 804 which is movable within the confines of the ring. The ball 804 has a diameter greater than the holes 802a, 806a in the septum layers 802, 806, respectively.

It will be understood that many other modifications can be made to the various disclosed embodiments without departing from the spirit and scope of the invention. For these reasons, the above description should not be construed as limiting the invention, but should be interpreted as merely exemplary of the disclosed embodiments.

The invention claimed is:

1. A surgical access device, comprising:
 a sealing valve for sealing across an incision in a patient, the sealing valve including at least a first sheet comprising an open edge, and a second sheet comprising an open edge;
 a sheath retractor couplable to the sealing valve;
 wherein the open edges of the first sheet and the second sheet are rotationally offset around an axial axis relative to each other;
 wherein the first sheet and the second sheet are movable relative to one another between a first state forming a zero seal in the absence of an instrument and a second state forming an instrument seal in the presence of an instrument;
 wherein in the first state, the open edge portions of the first sheet and the second sheet overlap each other; and
 wherein the surgical access device is configured to be coupled to the sheath retractor.

2. The surgical access device of claim 1, wherein at least one of the first sheet and the second sheet includes a gel material.

3. The surgical access device of claim 2, wherein: the first sheet includes a gel material; and the second sheet includes a gel material.

4. The surgical access device of claim 1, wherein the first sheet and the second sheet are biased toward the first state.

5. The surgical access device of claim 1, wherein the overlapping portions between the first sheet and the second sheet are substantially planar.

6. The surgical access device of claim 1, wherein at least one of the first sheet and the second sheet is substantially planar.

7. The surgical access device of claim 1, wherein the overlapping portions of the first sheet and the second sheet part during the introduction of an instrument within the overlapping portions.

8. The surgical access device of claim 1, wherein the sealing valve is configured to be located proximal to the incision in the patient.

9. The surgical access device of claim 1, further comprising a third sheet including a septum layer having a hole therethrough.

10. The surgical access device of claim 9, further comprising a fourth sheet including a septum layer having a hole therethrough, wherein the hole in the third sheet has a diameter substantially equal to a diameter of the hole in the fourth sheet.

11. A method of accessing an abdominal cavity through an incision in the abdominal wall, comprising:
   arranging the sealing valve of claim 1 across an incision in an abdominal wall;
   passing an instrument through the sealing valve, thereby converting the sealing valve to the second state; and
   advancing the instrument distally into an abdominal cavity.

12. The method of claim 11, further comprising positioning the sealing valve proximal to the incision.

13. The method of claim 11, further comprising:
   providing a sheath retractor;
   retracting the incision within the abdominal wall with the sheath retractor.

14. The method of claim 13, further comprising:
   coupling the sealing valve to the sheath retractor.

15. The method of claim 11, wherein the instrument is a surgeon's hand.

16. The method of claim 11, wherein the instrument is a surgical instrument.

17. A surgical access device comprising:
   a sealing valve for sealing across an incision in a patient, the sealing valve including at least a first sheet comprising an open edge, and a second sheet comprising an open edge;
   wherein the open edges of the first sheet and the second sheet are rotationally offset around an axial axis relative to each other;
   wherein the first sheet and the second sheet are movable relative to one another between a first state forming a zero seal in the absence of an instrument and a second state forming an instrument seal in the presence of an instrument; and
   wherein in the first state, the open edge portions of the first sheet and the second sheet overlap each other;
   further comprising a ring, wherein:
      the first sheet comprises a perimeter, a portion of which is secured to the ring, and
      the second sheet comprises a perimeter, a portion of which is secured to the ring.

18. The surgical access device of claim 17, wherein the first sheet and the second sheet are biased toward the first state.

19. The surgical access device of claim 17, further comprising a third sheet including a septum layer having a hole therethrough.

20. A surgical access device, comprising:
   a sealing valve for sealing across an incision in a patient, the sealing valve including at least a first sheet comprising an open edge, and a second sheet comprising an open edge;
   wherein the open edges of the first sheet and the second sheet are rotationally offset around an axial axis relative to each other;
   wherein the first sheet and the second sheet are movable relative to one another between a first state forming a zero seal in the absence of an instrument and a second state forming an instrument seal in the presence of an instrument; and
   wherein in the first state, the open edge portions of the first sheet and the second sheet overlap each other;
   further comprising a third sheet comprising an open edge and a fourth sheet comprising an open edge, wherein:
   the open edges of the third sheet and the fourth sheet are rotationally offset around an axial axis relative to each other; and
   wherein in the first state, the open edge portions of the third sheet and the fourth sheet overlap each other.

21. The surgical access device of claim 20, wherein at least one of the first sheet and the second sheet includes a gel material.

* * * * *